United States Patent
Hudson

(10) Patent No.: US 9,402,769 B1
(45) Date of Patent: Aug. 2, 2016

(54) INFANT HEADGEAR ASSEMBLIES

(71) Applicant: Katherine Louise Hudson, Chandler, AZ (US)

(72) Inventor: Katherine Louise Hudson, Chandler, AZ (US)

( * ) Notice: Subject to any disclaimer, the term of this patent is extended or adjusted under 35 U.S.C. 154(b) by 418 days.

(21) Appl. No.: 13/975,441

(22) Filed: Aug. 26, 2013

(51) Int. Cl.
*A61F 11/14* (2006.01)

(52) U.S. Cl.
CPC ...................................... *A61F 11/14* (2013.01)

(58) Field of Classification Search
CPC ....... A61F 5/055; A61F 5/05891; A61F 5/08; A61F 11/14; A61F 11/12; A61F 11/08; A61F 11/06; A45D 44/22; A61B 6/0421; A42B 3/166
See application file for complete search history.

(56) References Cited

U.S. PATENT DOCUMENTS

| | | | | |
|---|---|---|---|---|
| 5,495,853 A | * | 3/1996 | Yasushi | A61B 5/0482 600/27 |
| 6,986,167 B1 | * | 1/2006 | Coutant | A63B 71/10 2/425 |

* cited by examiner

*Primary Examiner* — Ophelia A Hawthorne
(74) *Attorney, Agent, or Firm* — Michael W. Goltry; Robert A. Parsons; Parsons & Goltry

(57) ABSTRACT

An infant headgear assembly includes elastic, nonslip anterior and posterior head straps on either side of an elastic, nonslip middle head strap that connect left and right earguard pads to provide noise suppression and ear protection. The left and right earguard pads and the anterior, posterior, and middle head straps cooperate to define a head-receiving volume to receive the head of an infant to position the left and right earguard pads over the left and right ears of the infant for noise suppression and ear protection purposes. The anterior, posterior, and middle head straps are to elastically stretch and extend across and nonslip contact frontal, occipital, and parietal regions, respectively, of the head of the infant to hold the left and right earguard pads in place, which are connecting points for operatively anchoring ventilation therapy devices relative to a face of the infant.

8 Claims, 12 Drawing Sheets

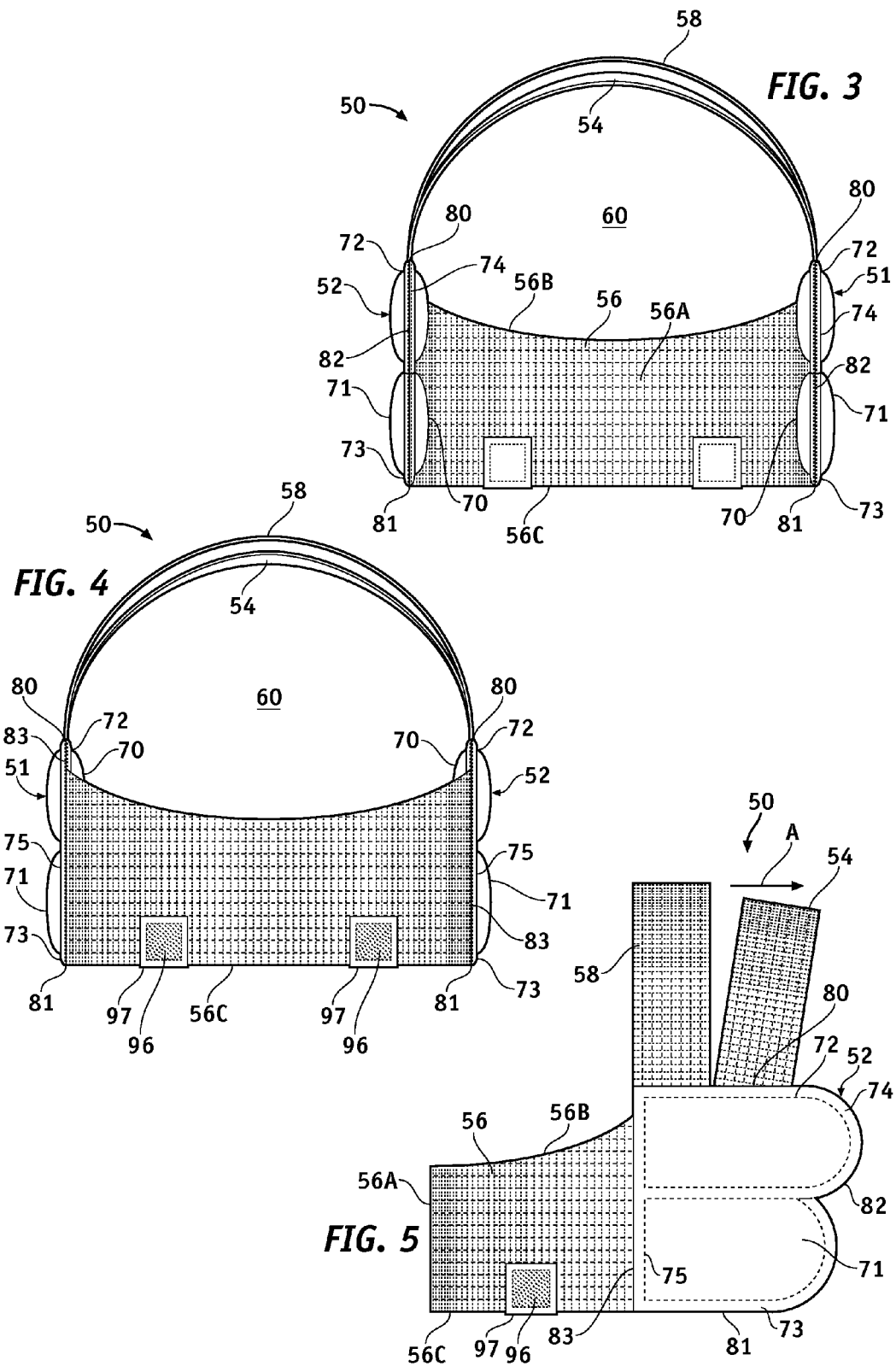

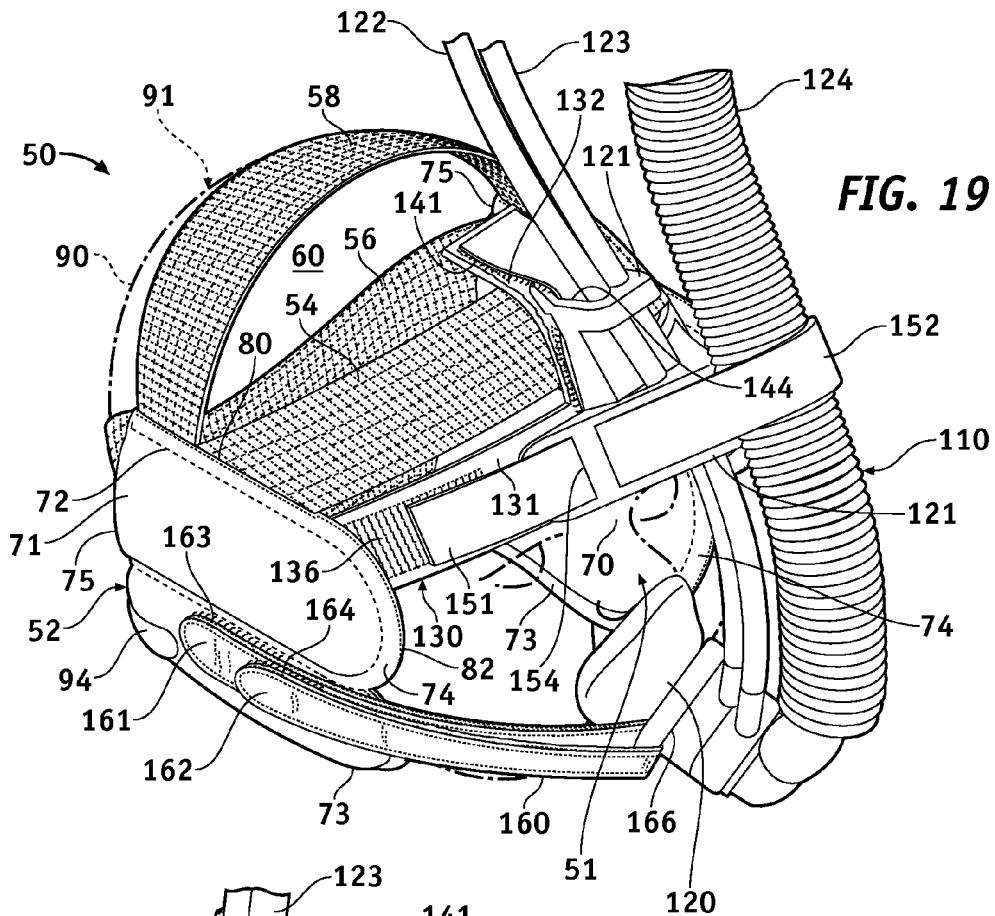
FIG. 19
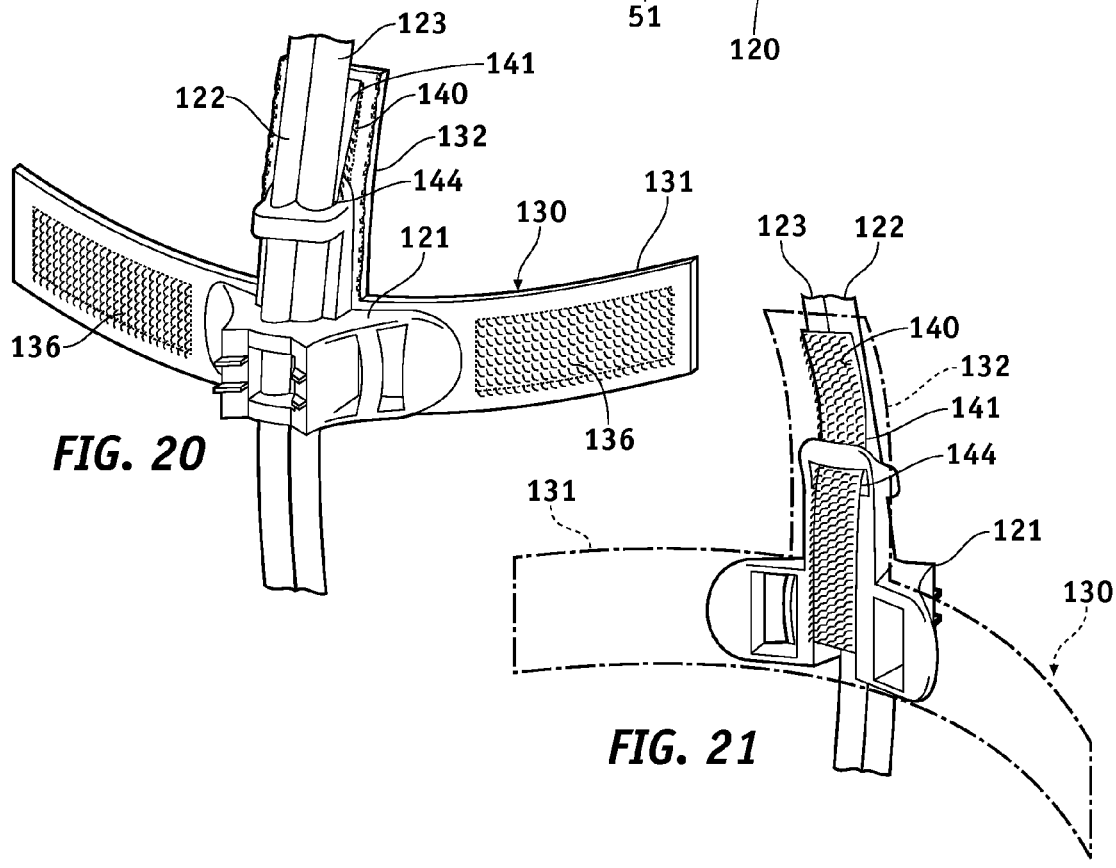
FIG. 20
FIG. 21

INFANT HEADGEAR ASSEMBLIES

FIELD OF THE INVENTION

The present invention relates to infant wear and, more particularly, to infant headgear useful for operatively anchoring therapy devices, such as ventilation therapy devices and phototherapy devices, relative to a face of an infant.

BACKGROUND OF THE INVENTION

Infants often suffer from neonatal jaundice, skin conditions, such as psoriasis, difficulty breathing when their lungs have not fully developed, and respiratory distress. These conditions are treatable. Neonatal jaundice and some skin conditions, such as psoriasis, are successfully treated with phototherapy treatment. Ventilation therapy, such as continuous positive airway pressure (CPAP) therapy, is useful to treat infants whose lungs have not fully developed. Nasal ventilation with a nasal cannula is useful to treat respiratory distress.

Phototherapy treatment is harmful to the eyes. Accordingly, the eyes of an infant must be shielded from the therapeutic light, such as with protective masks. Administration of ventilation therapy with CPAP devices and nasal cannulas requires that devices be held in place relative to the face of the infant to ensure the ventilation therapy is properly administered. Infants often become agitated when equipment is applied to their faces, and routinely claw and pull protective eye masks and ventilation equipment away from their faces during therapy treatments. To address the problem, there is a need in the art for infant headgear that is useful not only for operatively anchoring protective eye masks and ventilation equipment and the like relative to the face of an infant in the application of phototherapy and ventilation therapy and the like, but also for calming the infant during therapy sessions and making it difficult for the infant to remove such therapeutic accessories from their faces.

SUMMARY OF THE INVENTION

According to the principle of the invention, an infant headgear assembly for operatively anchoring infant therapy devices in the application of therapy to an infant includes left and right earguard pads to provide noise suppression and ear protection. The left and right earguard pads are soft and cushiony and each includes an inner side, an opposed outer side, a top, a bottom, a front, and a rear. An elongate anterior head strap, an elongate posterior head strap, and an elongate middle head strap between the anterior head strap and the posterior head strap all connect the left earguard pad to the right earguard pad. The left and right earguard pads and the anterior, posterior, and middle straps cooperate to define a head-receiving volume. The anterior head strap is connected to the top of the left earguard pad between the rear and the front, and is connected to the top of the right earguard pad between the rear and the front thereof. The entirety of the anterior head strap is made of pliant, elastic, nonslip material. The posterior head strap is connected to the rear of the left earguard pad between the top and the bottom thereof, and is connected to the rear of the right earguard pad between the top and the bottom thereof. The entirety of the posterior head strap is made of pliant, elastic, nonslip material. The middle head strap is connected to the top of the left earguard pad between the rear thereof and the anterior head strap, and is connected to the top of the right earguard pad between the rear thereof and the anterior head strap. The entirety of the middle head strap is made of pliant, elastic, nonslip material. The head-receiving volume is to receive a head of an infant to position the inner side of the left earguard pad against a left side of the head of the infant for left ear noise suppression and left ear protection, and to position the inner side of the right earguard pad against a right side of the head of the infant for right ear noise suppression and right ear protection, wherein the anterior head strap is to elastically stretch and extend across and nonslip contact a frontal region of the head of the infant from the left earguard pad to the right earguard pad, the posterior head strap is to elastically stretch and extend across and nonslip contact an occipital region of the head of the infant from the left earguard pad to the right earguard pad, the middle head strap is to elastically stretch and extend across and nonslip contact a parietal region of the head of the infant from the left earguard pad to the right earguard pad, and wherein the inner sides of the left and right earguard pads and the outer sides of the left and right earguard pads are available to releasably connect therapy devices for operatively anchoring therapy devices relative to a face of an infant. Such therapy devices include, for example, a mask for shielding the eyes of an infant during phototherapy treatment, and ventilation therapy devices, such as nasal cannulas and continuous positive air pressure (CPAP) devices, for delivering ventilation therapy to the infant. The middle head strap extends vertically upward relative to the tops of the left and right earguard pads. The posterior head strap extends horizontally rearward relative to the middle head strap from the rears of the left and right earguard pads. The anterior head strap extends angularly upward relative to the tops of the left and right earguard pads, and extends angularly forward relative to the middle head strap. The posterior head strap is connected to a majority of the rear of the left earguard pad from the bottom to the top thereof, and is connected to a majority of the rear of the right earguard pad from the bottom to the top thereof. The posterior head strap is of maximum width nearer the rears of the left and right earguard pads and is of minimum width at a middle of the posterior head strap between the rears of the left and right earguards. The posterior head strap includes a top edge and an opposed bottom edge, and the top edge is curved downwardly toward the bottom edge from the left and right earguard pads to the middle of the posterior head strap to relate to a curvature of the occipital region of the head of the infant. The anterior and middle head straps each have a maximum width that is less than the minimum width of the posterior head strap. A first connector releasably connected between the posterior head strap and one of the left and right earguard pads takes up a first length of the posterior head strap so as to shorten the posterior head strap. A second connector releasably connected between the posterior head strap and the other one of the left and right earguard pads takes up a second length of the posterior head strap so as to shorten the posterior head strap.

According to the principle of the invention, an infant headgear assembly for operatively anchoring infant therapy devices in the application of therapy to an infant includes left and right earguard pads to provide noise suppression and ear protection. The left and right earguard pads are soft and cushiony and each includes an inner side, an opposed outer side, and a parametric edge that includes an upper edge and a lower edge that extend between a rear edge and a front edge. An elongate anterior head strap, an elongate posterior head strap, and an elongate middle head strap between the anterior head strap and the posterior head strap all connect the left earguard pad to the right earguard pad. The left and right earguard pads and the anterior, posterior, and middle straps cooperate to define a head-receiving volume. The anterior head strap is connected to the upper edge of the left earguard pad between the rear edge and the front edge thereof, and is connected to the upper edge of the right earguard pad between the rear edge and the front edge thereof. The entirety of the anterior head strap is made of pliant, elastic, nonslip material. The posterior head strap is connected to the rear edge of the left earguard pad between the upper edge and the lower edge thereof, and is connected to the rear edge of the right earguard pad between the upper edge and the lower edge thereof. The entirety of the posterior head strap is made of pliant, elastic, nonslip material. The middle head strap is connected to the upper edge of the left earguard pad between the rear edge thereof and the anterior head strap, and is connected to the upper edge of the right earguard pad between the rear edge thereof and the anterior head strap. The entirety of the middle head strap is made of pliant, elastic, nonslip material. The head-receiving volume to receive a head of an infant to position the inner side of the left earguard pad against a left side of the head of the infant for left ear noise suppression and left ear protection, and to position the inner side of the right earguard pad against a right side of the head of the infant for right ear noise suppression and right ear protection, wherein the anterior head strap is to elastically stretch and extend across and nonslip contact a frontal region of the head of the infant from the left earguard pad to the right earguard pad, the posterior head strap is to elastically stretch and extend across and nonslip contact an occipital region of the head of the infant from the left earguard pad to the right earguard pad, the middle head strap is to elastically stretch and extend across and nonslip contact a parietal region of the head of the infant from the left earguard pad to the right earguard pad, and wherein the inner sides of the left and right earguard pads and the outer sides of the left and right earguard pads are available to releasably connect therapy devices for operatively anchoring therapy devices relative to a face of an infant. Such therapy devices include, for example, a mask for shielding the eyes of an infant during phototherapy treatment, and ventilation therapy devices, such as nasal cannulas and CPAP devices, for delivering ventilation therapy to the infant. The middle head strap extends vertically upward relative to the upper edges of the left and right earguard pads. The posterior head strap extends horizontally rearward relative to the middle head strap from the rear edges of the left and right earguard pads. The anterior head strap extends angularly upward relative to the upper edges of the left and right earguard pads, and extends angularly forward relative to the middle head strap. The posterior head strap is connected to a majority of the rear edge of the left earguard pad from the lower edge to the upper edge thereof, and is connected to a majority of the rear edge of the right earguard pad from the lower edge to the upper edge thereof. The posterior head strap is of maximum width nearer the rear edges of the left and right earguard pads and is of minimum width at a middle of the posterior head strap between the rear edges of the left and right earguards. The anterior and middle head straps each have a maximum width that is less than the minimum width of the posterior head strap. The posterior head strap includes a top edge and an opposed bottom edge, and the top edge is curved downwardly toward the bottom edge from the left and right earguard pads to the middle of the posterior head strap to relate to a curvature of the occipital region of the head of the infant. A first connector releasably connected between the posterior head strap and one of the left and right earguard pads takes up a first length of the posterior head strap so as to shorten the posterior head strap. A second connector releasably connected between the posterior head strap and the other one of the left and right earguard pads takes up a second length of the posterior head strap so as to shorten the posterior head strap.

BRIEF DESCRIPTION OF THE DRAWINGS

Referring to the drawings:

FIG. 3 is a front elevation view of the headgear assembly of FIG. 1;

FIG. 4 is a rear elevation view of the headgear assembly of FIG. 1;

FIG. 5 is a right side elevation view of the headgear assembly of FIG. 1, the opposing right side elevation view being the same thereof;

FIG. 19 is a right front perspective view of the embodiment of FIG. 18, with the head of the infant shown in phantom outline for illustrative purposes;

FIG. 20 is a fragmented outer side perspective view of ventilation therapy device of 19 illustrating a forehead anchor of the ventilation therapy device shown is a it would appear applied to a backing;

FIG. 21 is an underside perspective view of the embodiment of FIG. 20 with the backing shown in phantom outline for illustrative purposes;

DETAILED DESCRIPTION

Figure 1:
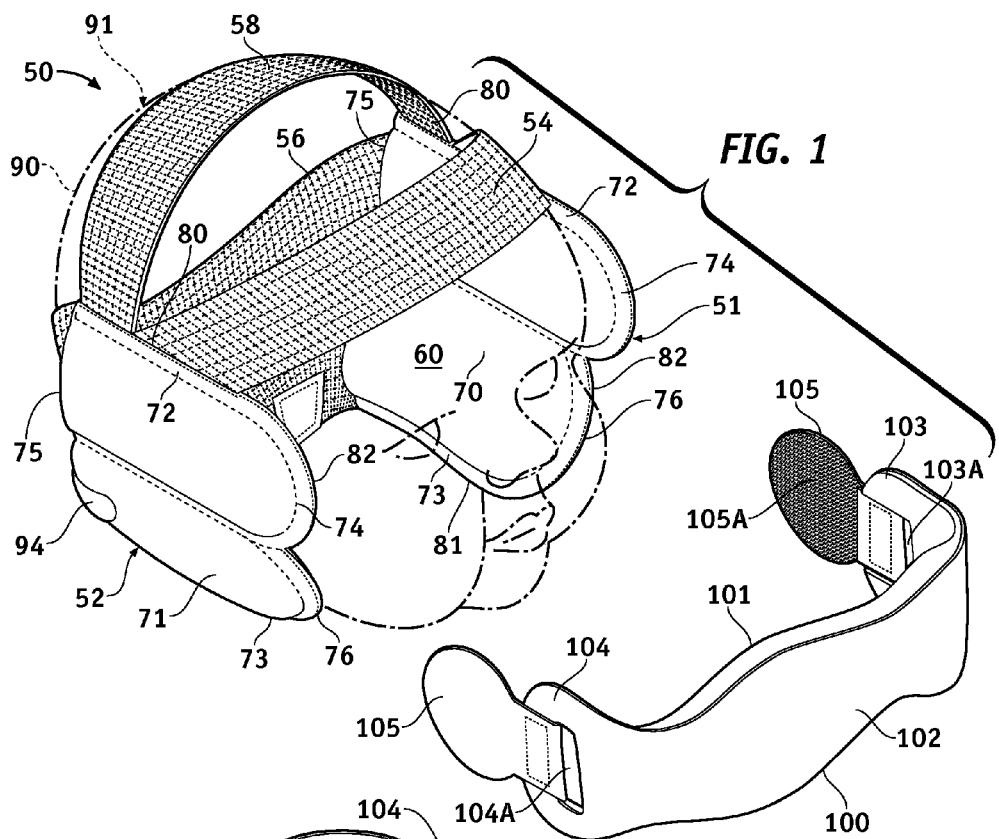
FIG. 1 is a right front perspective view of an infant headgear assembly constructed and arranged in accordance with the principle of the invention, and a mask shown as it would appear detached from the headgear assembly in preparation for being connected to the headgear assembly, the headgear assembly includes elastic, nonslip anterior and posterior head straps on either side of an elastic, nonslip middle head strap that connect left and right earguard pads to provide noise suppression and ear protection.
Figure 2:
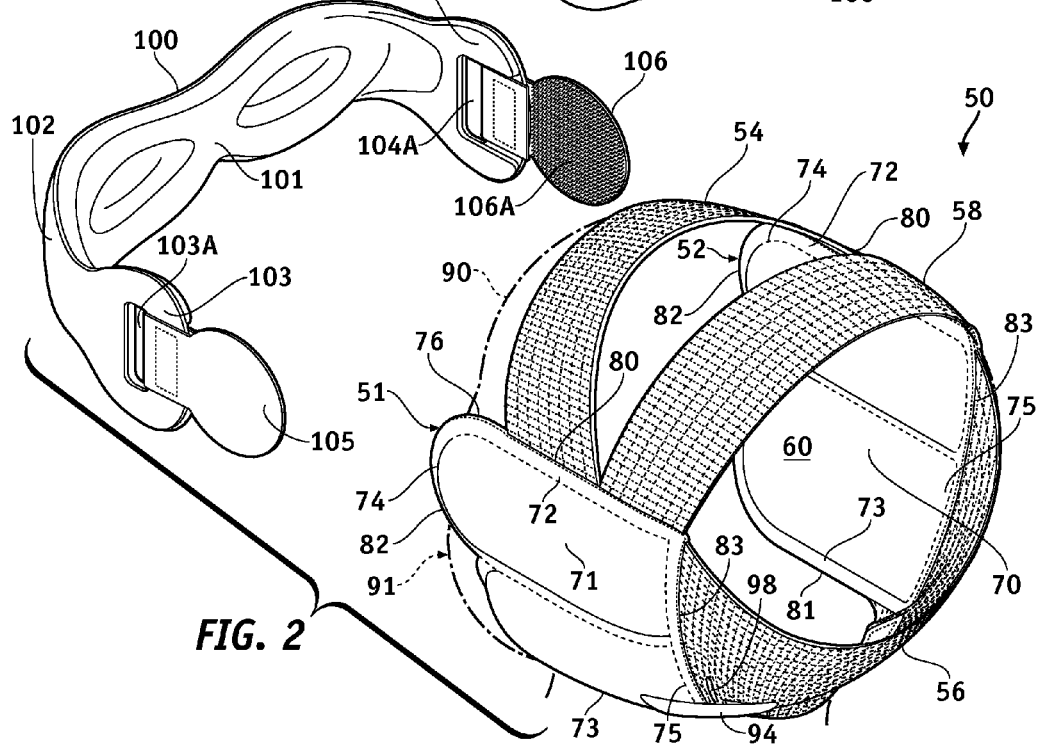
FIG. 2 is a left rear perspective view of the headgear assembly and the mask illustrated in FIG. 1.
Figure 6:
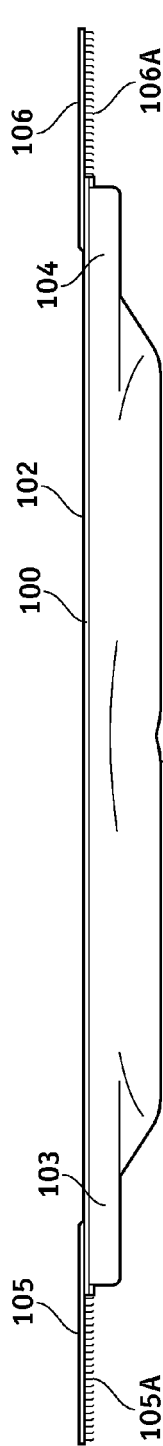
FIG. 6 is a top plan view of the mask of FIG. 1.

Turning now to the drawings, in which like reference characters indicate corresponding elements throughout the several views, attention is directed to FIG. 1 and FIG. 2 in which there is seen an infant headgear assembly 50 for operatively anchoring infant therapy devices relative to the face of an infant in the application of therapy to the infant, such as phototherapy treatment and ventilation therapy. Headgear assembly 50 includes left and right earguard pads 51 and 52 to provide noise suppression and ear protection, a flat and elongate anterior head strap 54, a flat and elongate posterior head strap 56, and a flat and elongate middle head strap 58 between anterior head strap 54 and posterior head strap 56 all connected to left and right earguard pads 51 and 52 attaching left earguard pad 51 to right earguard pad 52. Left and right earguard pads 51 and 52, anterior head strap 54, posterior head strap 56, and middle head strap 58 cooperate to define a head-receiving volume 60 to receive the head of an infant. When installed on the head of an infant according to the teachings of the invention, left and right earguard pads 51 and 52 serve as connecting points for connecting infant therapy devices for operatively anchoring infant therapy devices relative to the face of an infant in the application of therapy to the infant, such as phototherapy and ventilation therapy.

Left and right earguard pads 51 and 52 are the mirror image of one another and are identical in every respect. Accordingly, the details of right earguard pad 52 will now be discussed, with the understanding that the ensuing discussion of right earguard pad 52 applies equally to left earguard pad 51, and that reference numerals used in the description of right earguard pad 51 are also used throughout the specification and the drawings in connection with left earguard pad 51.

Looking in relevant part to FIG. 1, FIG. 3, FIG. 4, and FIG. 5, right earguard pad 52 is a cushion-like mass of soft material, such as cotton, polyester or other like or similar padding material, used for comfort and protection, and includes inner side 70, outer side 71, top 72, bottom 73, front 74, rear 75, and parametric edge 76, which is the border or outer boundary of right earguard pad 51. Parametric edge 76 includes upper edge 80 at top 72, lower edge 81 at bottom 73, front edge 82 at front 74, and rear edge 83 at rear 75. Inner and outer sides 70 and 71 of right earguard pad 52 each have a cloth or clothlike surface characteristic, meaning they each have an inherent surface characteristic or texture, formed by weaving, felting or the like in the nature of tufted, fluffy, hairlike or hairy threads. Inner and outer sides 70 and 71 each therefore have a surface characteristic that a hook fastener of the well-known type readily-available under the trademark VELCRO® can catch and cling to.

The entirety of anterior head strap 54, the entirety of posterior head strap 56, and the entirety of middle head strap 58 are each made of a material or combination of materials having pliant, elastic, and nonslip material characteristics. Anterior, posterior, and middle head straps 54, 56, and 58 are each pliant in that each is flexible and supple and yielding so as to be easily influenced. Anterior, posterior, and middle head straps 54, 56, and 58 are each elastic in that each is capable of returning to its original length and shape after being stretched, deformed, compressed, or expanded. Anterior, posterior, and middle head straps 54, 56, and 58 are each nonslip in that each reduces, resists, or otherwise prevents slipping against surfaces it contacts. A preferred material for anterior, posterior, and middle head straps 54, 56, and 58 is a well-known material found under one or more of the trademarks COFLEX and COFLEX•LF$^2$, owned by Andover Healthcare, Inc., a corporation organized under the laws of Massachusetts and having offices at 9 Fanaras Drive, Salisbury, Mass. 01952. This latex-free material is a quick-stick open cell foam that clings to itself, that is pliant, elastic, nonslip, water-resistant, soft and therefore comfortable on the skin, and that is thin and lightweight for added comfort and prolonged wear.

With continuing reference in relevant part to FIGS. 1-5, anterior head strap 54 is connected via sewing to top 72 of left earguard pad 51 between rear 75 and front 74 thereof, and is connected via sewing to top 72 of right earguard pad 52 between rear 75 and front 74 thereof. Posterior head strap 56 is connected via sewing to rear 75 of left earguard pad 51 between top 72 and bottom 73 thereof, and is connected via sewing to rear 75 of right earguard pad 52 between top 72 and bottom 73 thereof. Middle head strap 58 is, in turn, connected via sewing to top 72 of left earguard pad 51 between rear 75 thereof and the connection of anterior head strap 54 to top 72 of left earguard pad 51, and is connected via sewing to top 72 of right earguard pad 52 between rear 75 thereof and the connection of anterior head strap 54 to top 72 of right earguard pad 52. Posterior head strap 56 is connected to a majority of height/length of rear 75 of left earguard pad 51 from bottom 73 to top 72 thereof, and is connected to a majority of height/length of rear 75 of right earguard pad 52 from bottom 73 to top 72 thereof.

In a further and more specific aspect, anterior head strap 54 is connected via sewing to upper edge 80 at top 72 of left earguard pad 51 between rear edge 83 at rear 75 and front edge 82 at front 74 thereof, and is connected via sewing to upper edge 80 at top 72 of right earguard pad 52 between rear edge 83 at rear 75 and front edge 82 at front 74 thereof. Posterior head strap 56 is connected via sewing to rear edge 83 at rear 75 of left earguard pad 51 between upper edge 80 at top 72 and lower edge 81 at bottom 73 thereof, and is connected via sewing to rear edge 83 at rear 75 of right earguard pad 52 between upper edge 80 at top 72 and lower edge 81 at bottom 73 thereof. Middle head strap 58 is, in turn, connected via sewing to upper edge 80 at top 72 of left earguard pad 51 between rear edge 83 at rear 75 thereof and the connection of anterior head strap 54 to upper edge 80 at top 72 of left earguard pad 51, and is connected via sewing to upper edge 80 at top 72 of right earguard pad 52 between rear edge 83 at rear 75 thereof and the connection of anterior head strap 54 to upper edge 80 at top 72 of right earguard pad 52. The connection of anterior, posterior, and middle head straps 54, 56, and 58 to left and right earguard pads 51 and 52 via sewing forms what is considered a permanent connection of anterior, posterior, and middle head straps 54, 56, and 58 to left and right earguard pads 51 and 52. This permanent connection means that the connection is not readily separable, such as without cutting the sewing away rendering it useless for reuse. If desired, the connection of anterior, posterior, and middle head straps 54, 56, and 58 to left and right earguard pads 51 and 52 can be a removable connection, namely, a connection that joins anterior, posterior, and middle head straps 54, 56, and 58 to left and right earguard pads 51 and 52 in such a manner as to be readily separable. Posterior head strap 56 is connected to a majority of the height/length of rear edge 83 at rear 75 of left earguard pad 51 from lower edge 81 bottom 73 to upper edge 80 at top 72 thereof, and is connected to a majority of the length of rear edge 83 at rear 75 of right earguard pad 52 from lower edge 81 at bottom 73 to upper edge 80 at top 72 thereof.

Middle head strap 58 extends vertically upward from and relative to upper edges 80 and tops 72 of left and right earguard pads 51 and 52, respectively, posterior head strap 56 extends horizontally rearward relative to middle head strap 58 from rear edges 83 of rears 75 of left and right earguard pads 51 and 52. Anterior head strap 54 extends angularly upward relative to upper edges 80 of tops 72 of left and right earguard pads 51 and 52, and extends angularly forward relative to middle head strap in a direction of arrowed line A in FIG. 5 from rears 75 of left and right earguard pads 51 and 52 to fronts 74 of left and right earguard pads 51 and 52. As best illustrated in relevant part in FIGS. 3-5, when relaxed and not elastically stretched posterior head strap 56 is of maximum width nearer rear edges 83 and rears 75 of left and right earguard pads 51 and 52 and is of minimum width at a middle 56A of posterior head strap 56 between rear edges 83 and rears 75 of left and right earguards 51 and 52, and anterior and middle head straps 52 and 58 each have a maximum width that is less than the minimum width of posterior head strap 54. In this embodiment, when relaxed and un-stretched, the minimum width of posterior head strap 56 at middle 56A is approximately twice the maximum width of each of anterior and middle head straps 54 and 58. With these width characteristics of the various straps, posterior head strap 54 is therefore wider than each of anterior and middle head straps 52 and 58. Posterior head strap 54 includes a top edge 56B and an opposed bottom edge 56C. Top edge 56B is curved downwardly toward bottom edge 56C from left and right earguard pads 51 and 52 to middle 56A of posterior head strap 56 to relate to a curvature of the occipital region of the head of an infant.

Headgear assembly 50 is adapted to be worn by a head of an infant, and is used to operatively anchor infant therapy devices relative to the face of an infant in the application of therapy to the infant, such as phototherapy treatment and ventilation treatment. Headgear assembly 50 is slipped over head 90 of infant 91 as in FIGS. 1, 2, 10-12, and 14-16, and head 90 of infant 91 is denoted in phantom outline in FIGS. 1, 2, 10 and 11. Head-receiving volume 60 is to receive head 90 of infant 91 to position inner side 70 of left earguard pad 51 against a left side of head 90 of infant 91 and over and across the left ear of infant 91 for left ear noise suppression and left ear and left side-of-the-head protection, to position inner side 70 of right earguard pad 52 against a right side of head 90 of infant 91 and over and across the right ear of infant 91 for right ear noise suppression and right ear and right side-of-the-head protection, wherein left and right earguard pads 51 and 51 are positioned upright along the left and right sides of head 90 of infant 91 from lower edges 81 and bottoms 73 of left and right earguard pads 51 and 52 to upper edges 80 and tops 72 of left and right earguard pads 51 and 52, and extend forwardly along the left and right sides of head 90 of infant 91 from rear edges 83 and rears 75 of left and right earguard pads 51 and 52 near the back of head 90 of infant 91 to front edges 82 and fronts 74 of left and right earguard pads 51 and 52 near the face of head 90 of infant 91.

Figure 15:
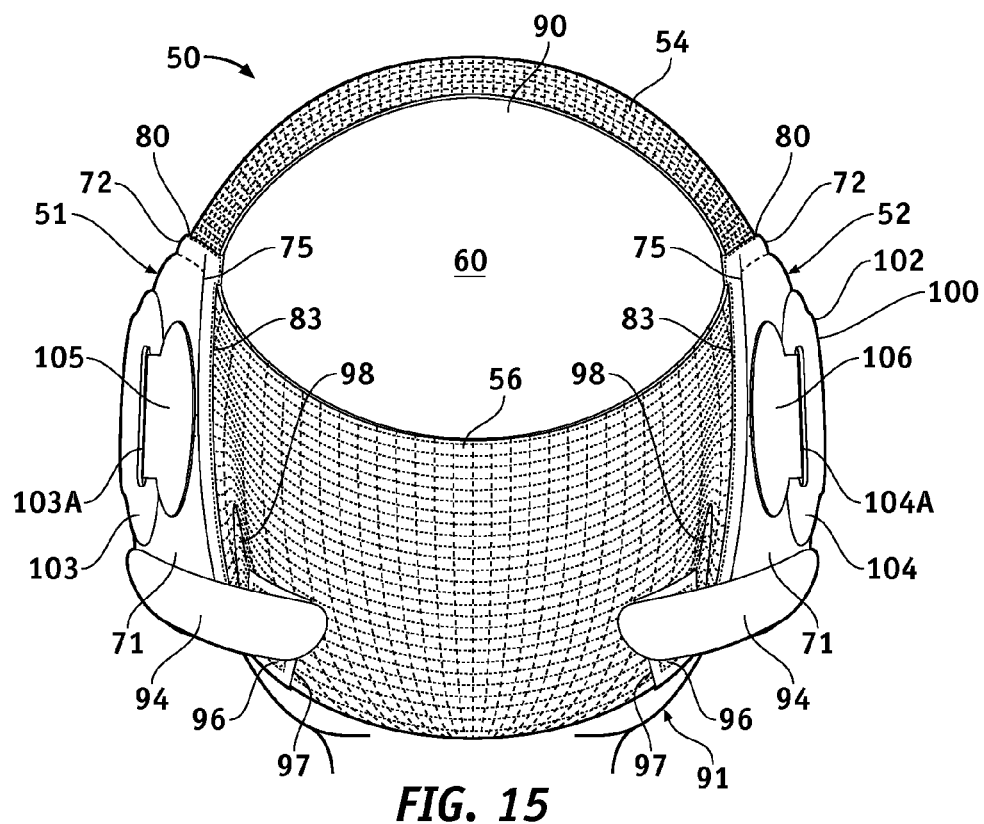
FIG. 15 is a rear elevation view of the embodiment of FIG. 12.

The lengths of anterior, posterior, and middle head straps 54, 56, and 58 causes them to elastically stretch over the head 90 of infant 91 when headgear assembly 50 is slipped onto head 90 of infant 91. Anterior head strap 54 angled upward and forwardly of middle head strap 58 is to elastically stretch and extend across and nonslip contact a frontal region of head 90 of infant 91 from left earguard pad 51 to right earguard pad 52, posterior head strap 56 is to elastically stretch and extend across and nonslip contact an occipital region or base of head 90 of infant 91 from left earguard pad 51 to right earguard pad 52, and middle head strap 58 between anterior and posterior head straps 54 and 56 is to elastically stretch and extend across and nonslip contact a parietal region of head 90 of infant 91, between the frontal and occipital regions of head 90 of infant 91, from left earguard pad 51 to right earguard pad 52. Anterior head strap 54 elastically constricts against and across the frontal region of head 90 of infant 91 and nonslip contacts the front region of head 90 of infant 91 from left earguard pad 51 to right earguard pad 52, posterior head strap 56 elastically constricts against and across the occipital region of head 90 of infant 91 and nonslip contacts the occipital region of head 90 of infant 91 from left earguard pad 51 to right earguard pad 52, and middle head strap 58 elastically constricts against and across the parietal region of head 90 of infant 91 and nonslip contacts the parietal region of head 90 of infant 91 from left earguard pad 51 to right earguard pad 52. FIG. 15 illustrates top edge 56B of posterior head band 56 curved downwardly toward bottom edge 56C from left and right earguard pads 51 and 52 to middle 56A of posterior head strap 56 to relate to the curvature of the occipital region of head 90 of infant 91.

The elasticity of anterior, posterior, and middle head straps 54, 56, and 58 elastically constrict headgear assembly 50 to head 90 of infant 91 and elastically constrict/draw left and right earguard pads 51 and 52 against the left and right ears and the left and right sides of head 90 of infant 91 providing the left and right ears with noise suppression and protecting the left and right sides of head 90 of infant 91 from being scratched or otherwise subjected to contact with external objects. The nonslip material characteristics of anterior, posterior, and middle head straps 54, 56, and 58 reduces, resists, or prevents anterior, posterior, and middle head straps 54, 56, and 58 from slipping against the surfaces they contact, namely, the surfaces of the frontal, occipital, and parietal regions of head 90 of infant 91. The three points of contact between headgear assembly 50 and head 90 of infant between left and right earguard pads 51 and 52 defined by the contact between anterior head strap 54 and the surface of the frontal region of head 90 of infant, the contact between posterior head strap 56 and the surface of the occipital region of head 90 of infant 91, and the contact between middle head strap 58 and the surface of the parietal region of head 90 of infant 91, together with the elastically constricting and nonslip material characteristics of anterior, posterior, and middle head straps 54, 56, and 58 provide a tight yet comfortable installation of headgear assembly 50 onto head 90 of infant 91, and make it substantially impossible for the infant 91 to remove headgear assembly 50 without the assistance of a caregiver. The width characteristics of posterior head strap 56 relative to anterior and middle head straps 54 and 58 produce an unexpected result of making it substantially impossible for the infant 91 to remove headgear assembly 50 by infant 91 reaching up with his hands and attempting to pulling anterior head strap 54 downwardly along his face because of the wide coverage of posterior head strap 56 across the occipital region of head 90 of infant 91. Even when elastically stretched the width characteristics of posterior head strap 56 relative to anterior and middle head straps 54 and 58 persist.

So installed, the material characteristics of anterior, posterior, and middle head straps 54, 56, and 58 make them soft and comfortable on the skin of the frontal, occipital, and parietal regions of head 90 of infant 91, left and right earguard pads 51 and 52 held against the left and right ears and the left and right sides of head 90 of infant importantly provide noise suppression to calm infant 91 during therapy sessions and protect the left and right sides of head 90 of baby 91 from direct contact with external objects, including the hands and fingers of infant 91, and are soft and comfortable against head 90 of infant 91, and left and right earguard pads 51 and 52 are useful contact points for releasably connecting therapy devices for operatively anchoring therapy devices relative to the face of infant 91. The contact points include inner side 70 and outer side 71 of each one of left and right earguard pads 51 and 52. Inner side 70 and outer side 71 of each one of left and right earguard pads 51 and 52 are completely free of obstructions and anterior, posterior, and middle head straps 54, 56, and 58 so as to be completely and totally available and contact points in the attachment of therapeutic or therapy devices/accessories.

Figure 17:
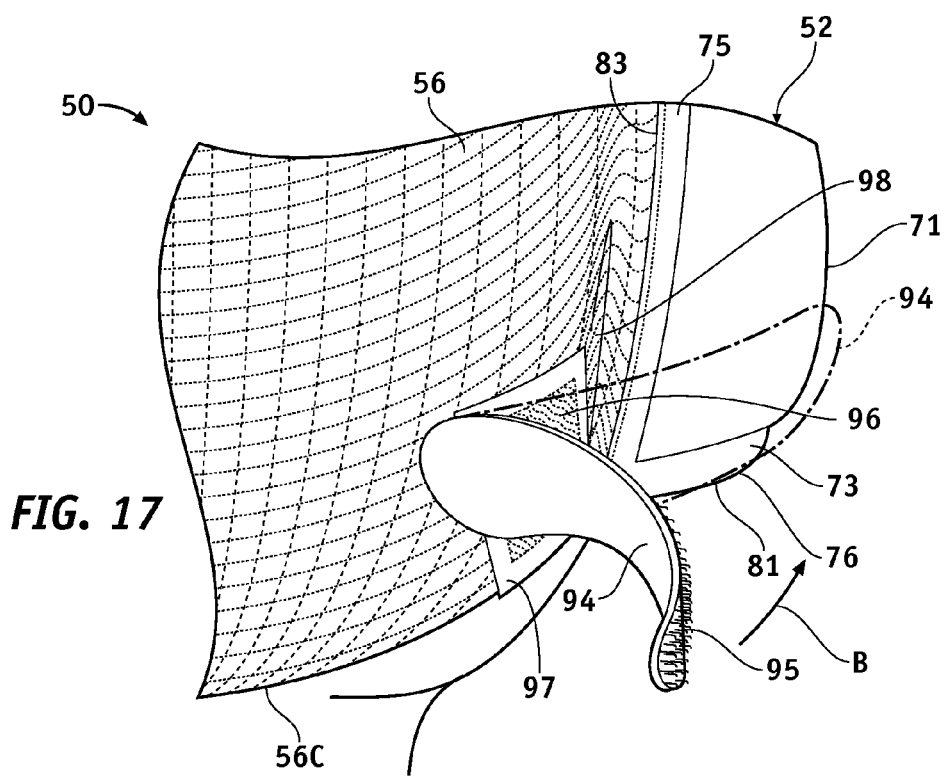
FIG. 17 is an enlarged, fragmented perspective view of the embodiment of FIG. 1 illustrating a connector as it would appear partially installed between the posterior head strap and the right earguard pad for taking up a length of the posterior head strap.
Figure 18:
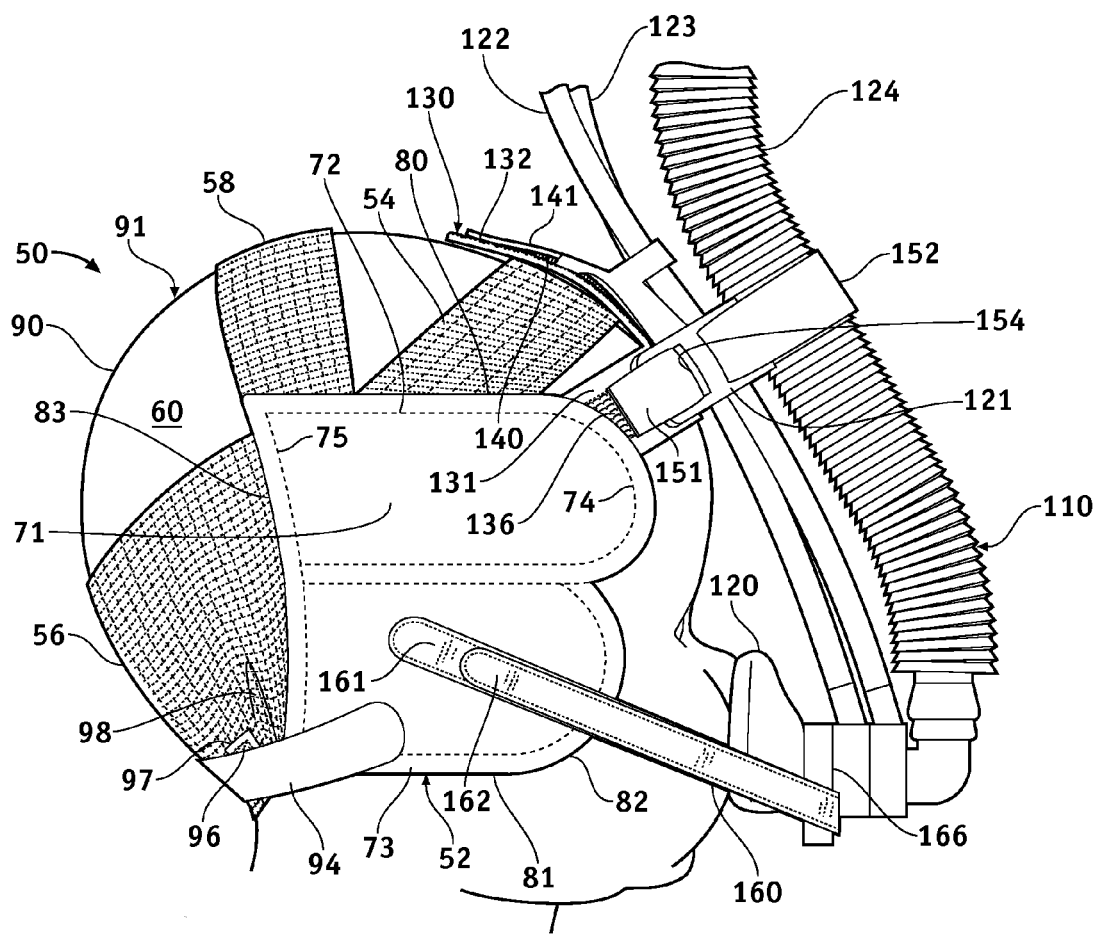
FIG. 18 is right side elevation view of the headgear assembly of FIG. 1 shown as it would appear worn by a head of an infant, and a ventilation therapy device shown as it would appear operatively anchored to the headgear assembly relative to the face of the infant for providing ventilation therapy, the ventilation therapy device consisting of a ventilation mask, a forehead anchor, and ventilation tubing connected between the ventilation mask and the forehead anchor for supplying ventilating air to the ventilation mask.
Figure 22:
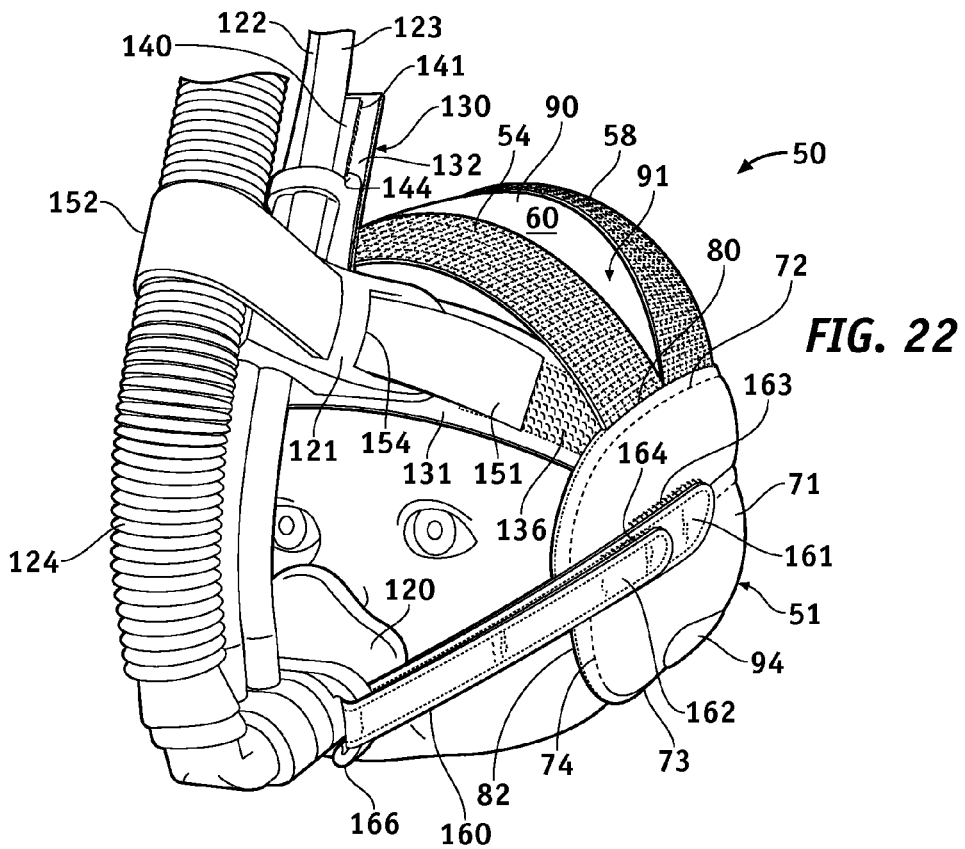
FIG. 22 is a left front perspective view of the embodiment of FIG. 18.

The length of posterior head strap 58 between left and right earguard pads 51 and 52 may be adjusted with a strap shortening assembly in order to adjust headgear assembly 50 to fit smaller infant heads or to otherwise increase the elastic tension applied across posterior head strap 56. Referring to FIG. 17, the strap shortening assembly includes a connector 94 that consists of a lineal strip or piece of fabric tape or other substrate with a hook fastener 95 formed on one side. Hook fastener 95 is the well-known type sold under the trademark VELCRO®, which catch in the loops of loop fasteners and the clothlike tufted threads/hairs of surfaces to fasten or bind temporarily, or otherwise to releasably fasten or connect. A corresponding loop fastener 96, also of the well-known type sold under the trademark VELCRO®, is carried by a piece of tape or other substrate 97 affixed via sewing and/or adhesive to the outer side of posterior head strap 56 near bottom edge 56C of posterior head strap 56 near rear 75 of right earguard pad 52.

Figure 7:
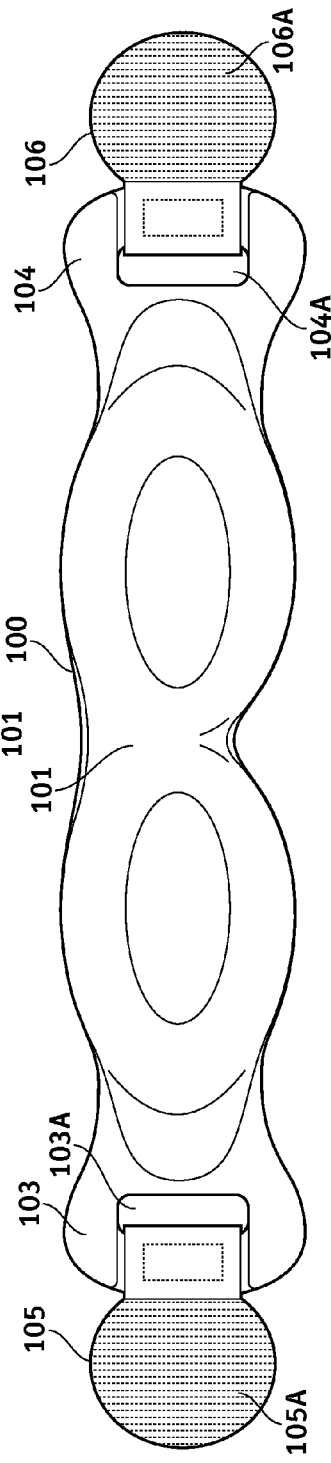
FIG. 7 is a front elevation view of the mask of FIG. 1.
Figure 8:
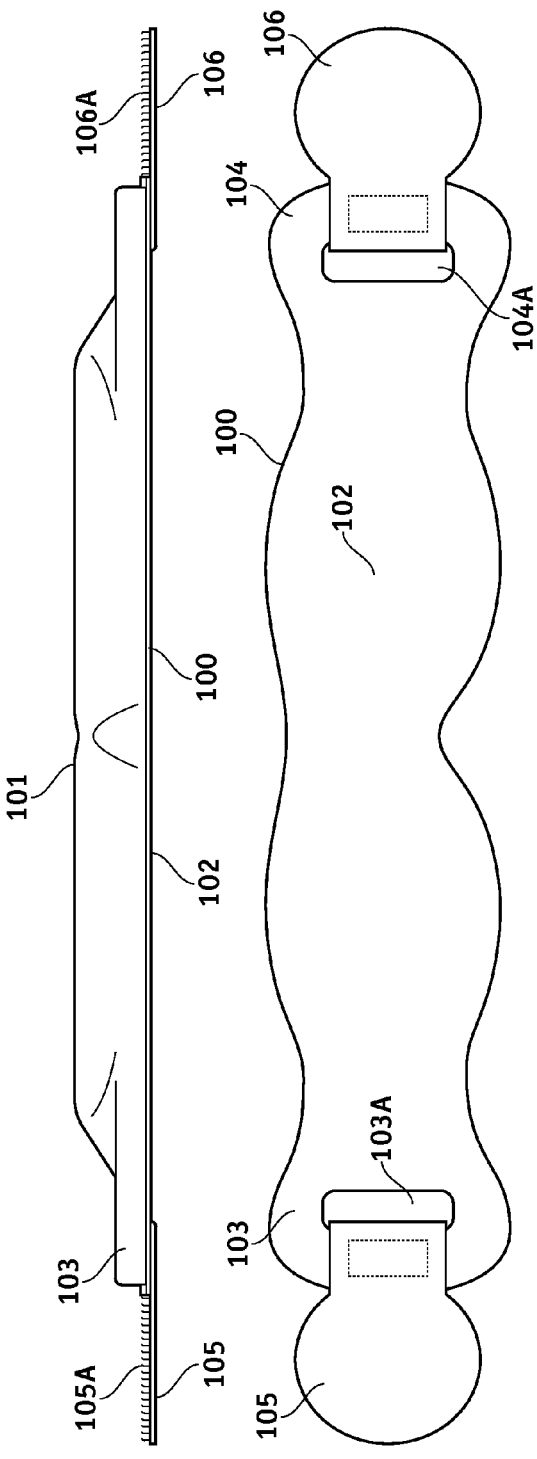
FIG. 8 is a bottom plan view of the mask of FIG. 1.
Figure 9:
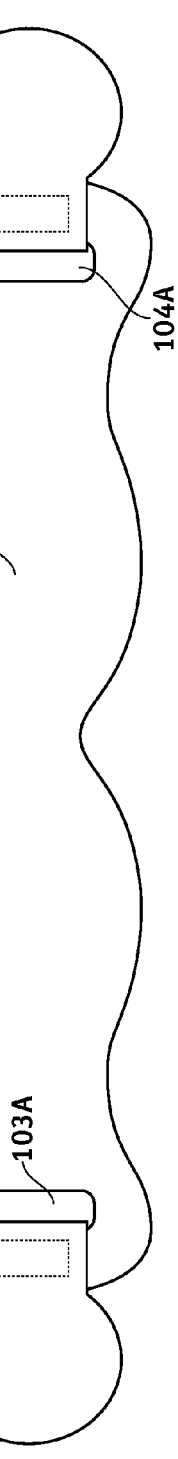
FIG. 9 is a rear elevation view of the mask of FIG. 1.
Figure 11:
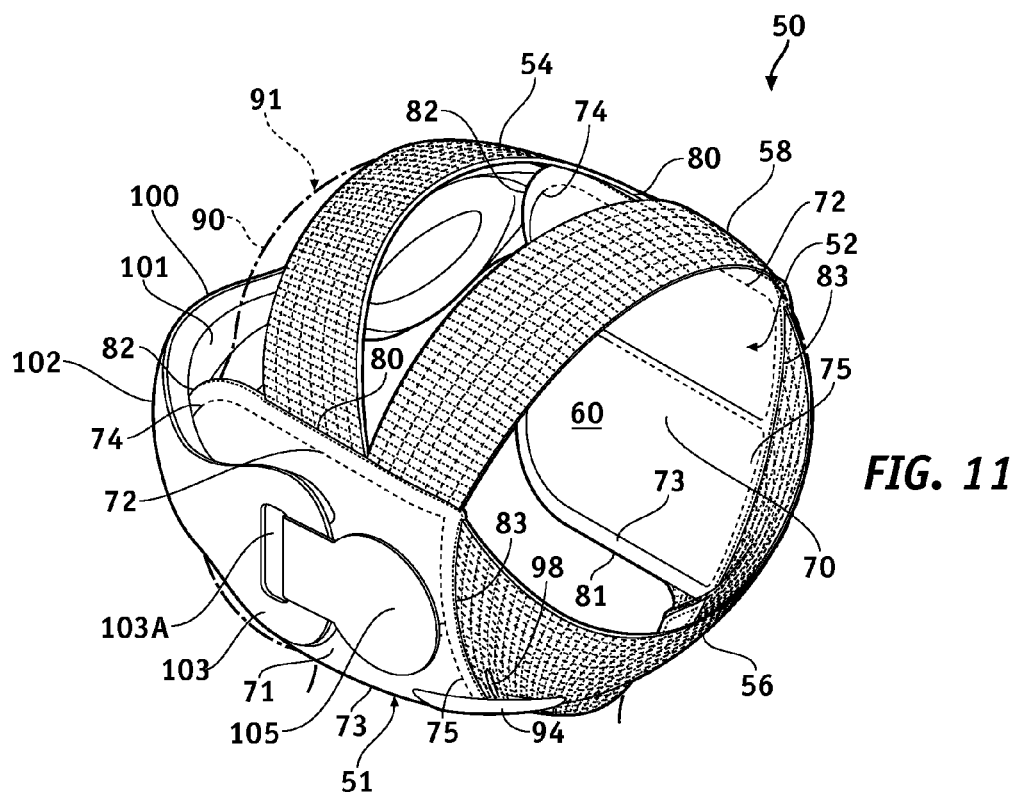
FIG. 11 is a rear left perspective view of the embodiment of FIG. 10.
Figure 12:
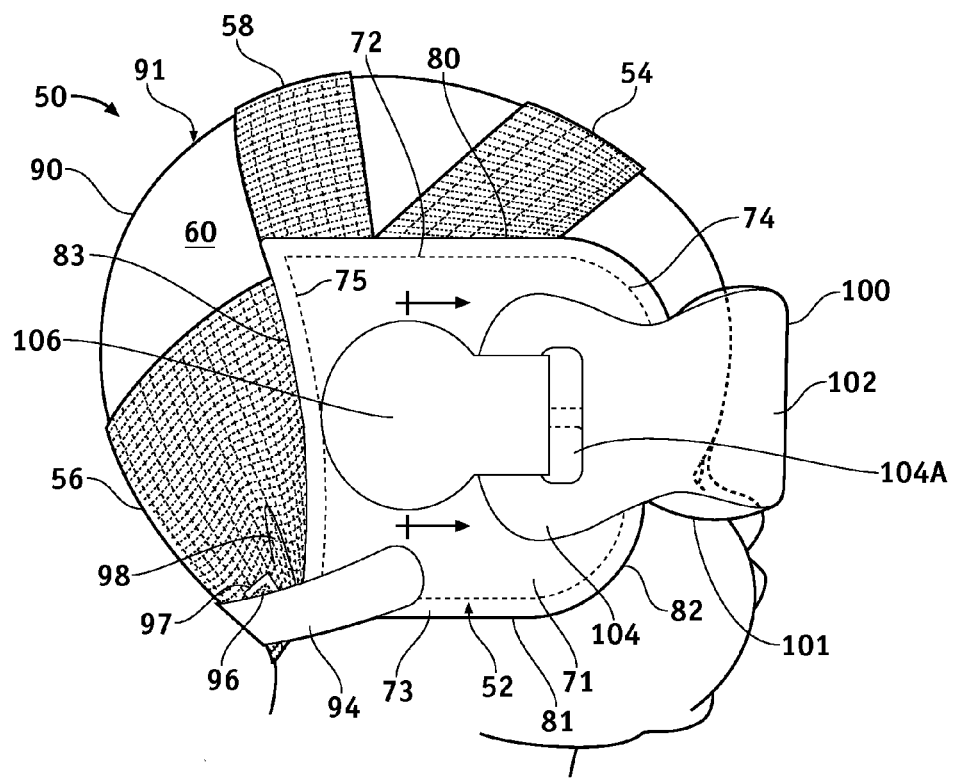
FIG. 12 is a right side elevation view of the embodiment of FIG. 10 illustrating the headgear assembly and the mask shown as they would appear worn by a head of an infant.

To shorten the length of posterior head strap 58 between left and right earguard pads 51 and 52, a fold or pleat 98 is formed in posterior head strap 56 between hook fastener 96 and right earguard pad 52 to take up a length of posterior head strap 56, hook fastener 95 is applied to loop fastener 96 temporarily/releasably fastening one end of connector 94 to posterior head strap 56, and the opposite end of connector 94 is then moved toward outer side 71 right earguard pad 52 in the direction of arrowed line B and hook fastener 95 pressed against outer side 71 of right earguard pad 52 as indicated by the position of connector 94 denoted in phantom outline in FIG. 7 temporarily/releasably fastening connector 94 to outer side 71 of right earguard pad 52 as in FIG. 12. This holds and maintains the taken up length of posterior head strap 56 defined by fold or pleat 98 to shorten the length of posterior head strap 56 between left and right earguard pads 51 and 52 in order to adjust headgear assembly 50 to fit smaller infant heads or to otherwise increase the elastic tension applied across posterior head strap 56. Again, hook fastener 95 catches the threads of outer face 71 of right earguard pad 52 to temporarily/releasably fasten or bind connector 94 to outer surface 71 of right earguard pad 52. To remove connector 94, connector 94 need only be torn away, such as by hand. An identical strap shortening assembly, including connector 94 and loop fastener 96 carried by substrate 97, may be formed between left earguard pad 51 and posterior head strap 56, as is shown in relevant part in FIGS. 2, 4, 11, and 15, to further shorten posterior head strap 56. FIGS. 2, 11, and 15 show connector 94 releasably connected between posterior head strap 56 and left earguard pad 51 taking up a length of posterior head strap 56 in the form of fold or pleat 98 so as to shorten the length of posterior head strap 56 between left and right earguard pads 51 and 52. An identical strap shortening assembly can be similarly formed between anterior head strap 64 and left earguard pad 51 and/or between anterior head strap 54 and right earguard pad 52, and between middle head strap 58 and left earguard pad 51 and/or between middle head strap 58 and right earguard pad 52.

As explained above, the COFLEX® brand material of anterior, posterior, and middle head straps 54, 56, and 58 clings to itself. To shorten the lengths of anterior, posterior, and middle head straps 54, 56, and 58, the straps can each be folded against itself, or cut in half and the free ends folded over one another and then pressed together.

As previously stated, left and right earguard pads 51 and 52 are useful contact points for releasably connecting therapy devices for operatively anchoring therapy devices relative to the face of infant 91, which will now be discussed. In FIGS. 1 and 2 there is seen a mask 100, which when attached to headgear assembly 50 is worn to cover and conceal the eyes of infant 91, such as during phototherapy treatment, which some infants require in order to treat certain conditions, such as neonatal jaundice, and certain skin conditions, such as psoriasis. Referencing FIGS. 1 and 2, and FIGS. 6-9 in relevant part, mask 100 is formed of soft, flexible material that is comfortable when worn. Mask 100 is elongate and has inner face 101 that is contoured to be received over the eyes of an infant to cover and conceal the eyes of an infant, outer face 102, and opposed outer ends 103 and 104. Connector 105 is connected to a slot opening 103A in outer end 103, and connector 106 is connected to a slot opening 104A in outer end 104. Connectors 105 and 106 are each a patch of fabric tape or other substrate. The inner side of connector 105 is a hook fastener 105A, and the inner side of connector 106 is a hook fastener 106A. Each hook fastener is the well-known type sold under the trademark VELCRO® as discussed above which catches in the loops of loop fasteners and the fluffy threads of clothlike tufted threads to fasten or bind temporarily.

Figure 10:
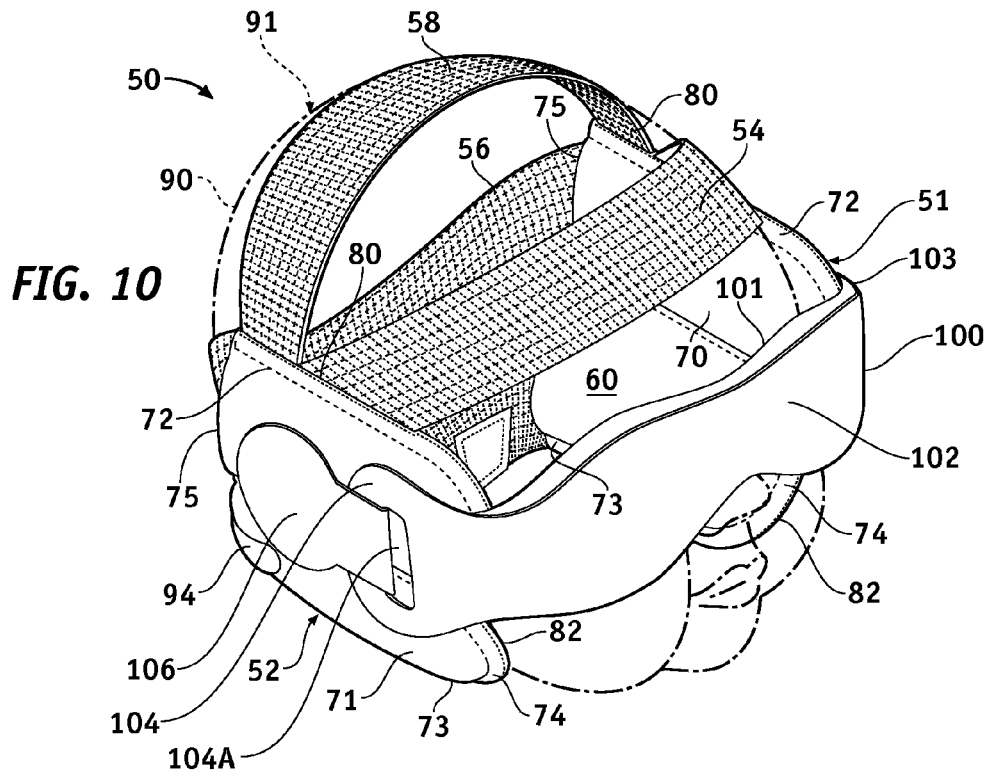
FIG. 10 is front right perspective view of the headgear assembly and the mask of FIG. 1 shown as they would appear connected and worn by a head of an infant depicted in phantom outline.
Figure 13:
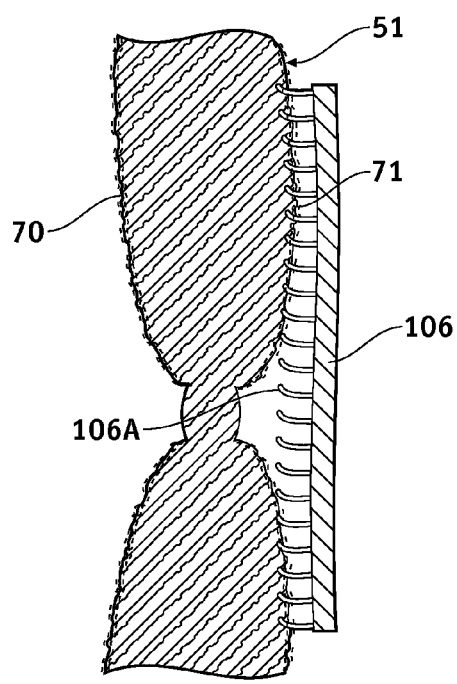
FIG. 13 is a section view taken along line 13-13 of FIG. 12.
Figure 14:
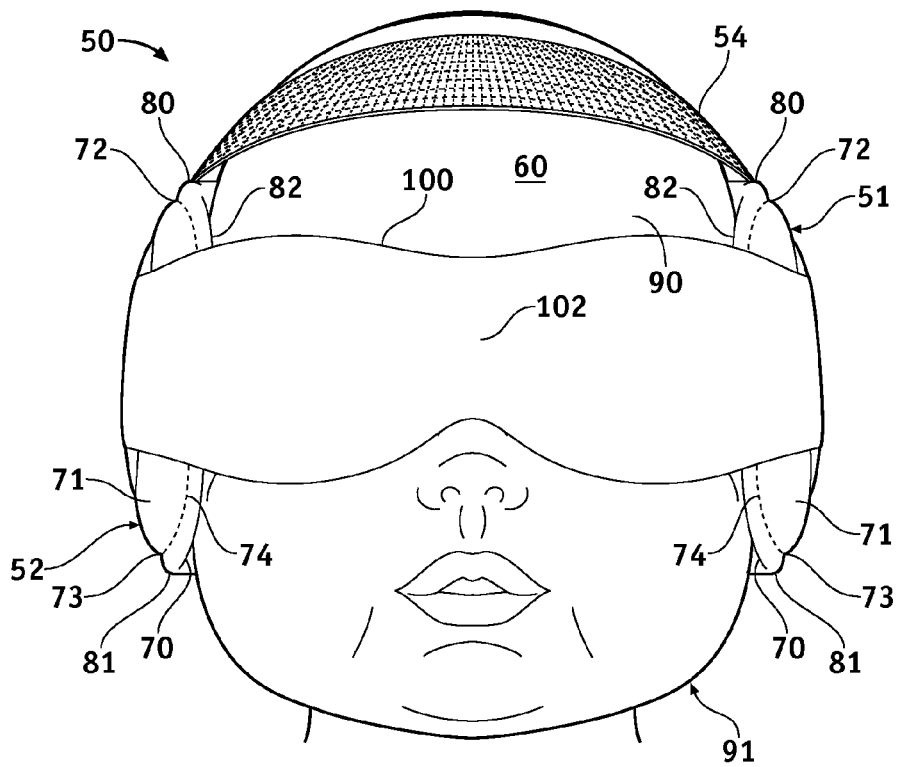
FIG. 14 is a front elevation view of the embodiment of FIG. 12.
Figure 16:
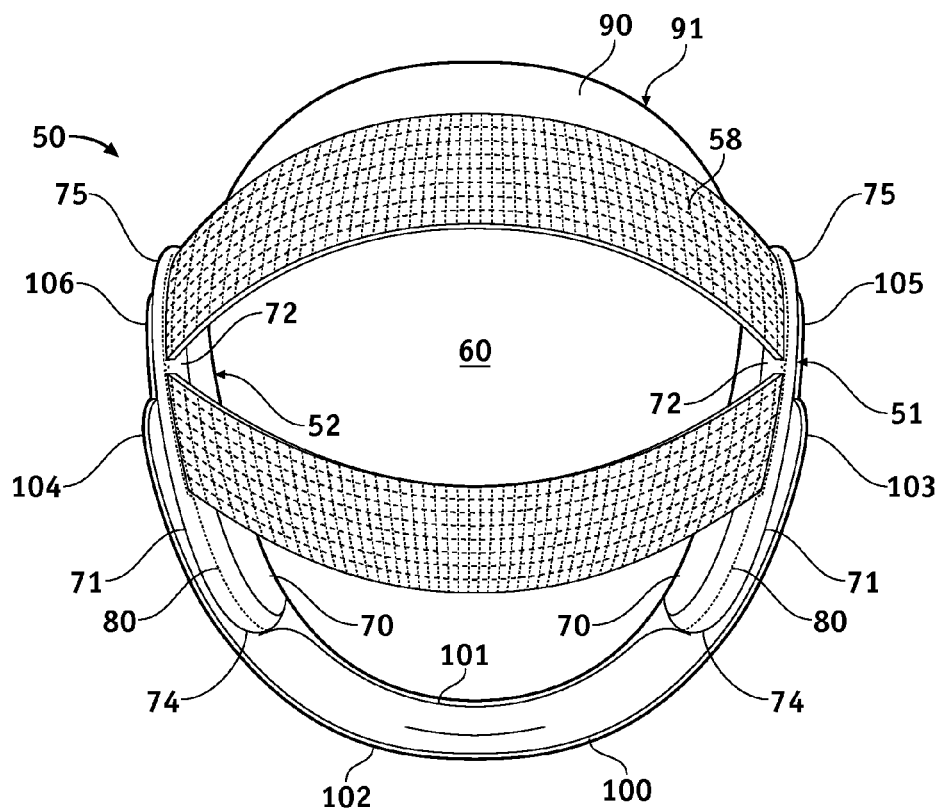
FIG. 16 is a top plan view of the embodiment of FIG. 12.

To install mask 100 to headgear assembly 50 when worn as in FIGS. 1 and 2 and also in FIGS. 10 and 11, inner face 101 is applied across the face of infant 91 to cover and conceal his eyes as in FIGS. 10 and 11, outer end 103 is bent around the left side of head 90 of infant 91 hook fastener 105A (shown in FIG. 1) of connector 105 is pressed against outer side 71 of left earguard pad 51 temporarily/releasably fastening connector 105 to outer side 71 of left earguard pad 51 as in FIG. 11, and outer end 104 is bent around the right side of head 90 of infant 91 and hook fastener 106A (shown in FIG. 2) of connector 106 is pressed against outer side 71 of right earguard pad 52 temporarily/releasably fastening connector 106 to outer side 71 of right earguard pad 52 as in FIG. 10 and FIG. 12. The clothlike threaded/tufted surface characteristic of outer surfaces 71 of left and right earguard pads 51 and 52 are caught by hook fastener 105A of connector 105 to temporarily/releasably bond to outer surface 71 of left earguard pad 51 and permit loop fastener 106A of connector 106 to temporarily/releasably bond to outer surface 71 of right earguard pad 52. For illustration and reference, FIG. 13 is a section view taken along line 13-13 of FIG. 12 illustrating loop fastener 106A of connector 106 as it would appear temporarily/releasably fastened to outer surface 71 of right earguard pad 52. FIG. 14 is a front elevation view of headgear 50 as would be worn by head 90 of infant 91 and mask 100 as it would appear connected to headgear assembly 50 so as to be operatively anchored relative to the face of infant 91 to cover and shield his eyes in preparation for phototherapy treatment. FIG. 15 is a rear elevation view of the embodiment of FIG. 14, and FIG. 16 is a top plan view of the embodiment of FIG. 14. With mask 100 so installed, infant 91 may be then be exposed to phototherapy treatment. During this treatment, mask 100 isolates and protects the eyes of infant 91 from the uncomfortable and/or damaging effects of the therapeutic light. The space between anterior and middle straps 54 and 58 and the space between middle strap 58 and posterior strap 54 expose portions of head 90 of infant 91 to the therapeutic light. To remove mask 100, connectors 105 and 106 need only be torn away from left and right earguard pads 51 and 52. The assembly of mask 100 to headgear assembly 50 forms an exemplary embodiment of the invention.

FIGS. 18, 19, 22, and 23 illustrate headgear assembly 50 as it would appear worn by head 90 of infant 91 in the manner as described above, and further shown in use operatively anchoring another form of therapy device relative to the face of infant 91 consisting of a well-known continuous positive air pressure (CPAP) device 110 that includes the customary ventilation mask 120, forehead anchor 121, and ventilation tubing connected between ventilation mask 120 and forehead anchor 121 for supplying ventilation therapy via ventilation mask. The ventilation tubing includes tubes 122 and 123, and corrugated tube 124.

FIG. 20 is a fragmented outer side perspective view of CPAP device 110 illustrating forehead anchor 121 applied to a backing 130 formed of flat, soft, flexible material, such as flat soft, flexible cloth or clothlike material that a hook fastener can catch and cling to. Backing 130 includes a horizontal part 131 and a vertical part 132 extending vertically upright from a middle of horizontal part 131. A hook fastener 136 of the well-known type sold under the trademark VELCRO® is applied to the outer side of each of the opposed ends of horizontal part 131. Looking also to FIG. 21, a hook fastener 140, again of the well-known type sold under the trademark VELCRO®, is carried by an elongate piece of fabric tape or other substrate 141 positioned on the underside of forehead anchor 121. Substrate 141 is threaded through slotted opening 144 of forehead anchor 121, and hook fastener 140 is, in turn, pressed against the outer side of vertical part 132 and the outer side of the middle of horizontal part 131 between hook fasteners 136 temporarily/releasably fastening substrate 141 to the outer side of backing 130 in turn releasably connecting forehead anchor 121 to backing 130 between hook fasteners 136. FIG. 21 is an underside perspective view of forehead anchor 121 releasably connected to backing 130, with backing 130 shown in phantom outline for illustrative purposes.

Looking in relevant part to FIGS. 18, 19, 22 and 23, with forehead anchor 121 releasably connected to the outer side of backing 130, backing 130 is releasably connected to headgear assembly 50 to operatively anchor forehead anchor 121 relative to the face of head 90 of infant 91. Specifically, inner side of backing 130 is applied directly against the forehead of head 90 of infant 91. Horizontal part 131 extends across infant's 91 forehead from left earguard pad 51 to right earguard pad 52, and vertical part 132 extends upright from horizontal part 131 and is applied across the outer side of anterior head strap 54. The outer ends of horizontal part 131 of backing 130 are tucked under inner sides 70 of left and right earguard pads 51 and 52 at fronts 74 of left and right earguard pads 51 and 52 near tops 72, respectively. Left and right earguard pads 51 and 52 are pressed against the outer ends of horizontal part 131 of substrate so as to press inner sides 70 of left and right earguard pads 51 and 52 against the respective hook fasteners 136 temporarily/releasably fastening the outer ends of horizontal part 131 of backing 130 to inner sides 70 of left and right earguard pads 51 and 52 in turn releasably connecting backing 130 to headgear assembly and, in turn, releasably connecting forehead anchor 121 to headgear assembly 50. The installation of backing 130 to headgear assembly 50 forms an exemplary embodiment of the invention. A portion of each loop fastener 136 is exposed on either side of forehead anchor 121. Backing 130 positioned between the forehead of head 90 of infant 91 and forehead anchor 121 isolates forehead anchor 121 from directly contacting head 90 of infant 91 to ensure the comfort of infant 91. If desired, vertical part 132 extending upright from horizontal part 131 can be applied under anterior head strap 54 and then hook fastener 140 of substrate 141 may, in turn, be pressed against the outer side of anterior head strap 54 and vertical part 132 on either side of anterior head strap 54 so as to temporarily/releasably fasten substrate 141 to vertical part 132. This arrangement captures anterior head strap 54 between vertical part 132 on the underside of anterior head strap 54 and substrate 141 on the outer side of anterior head strap 54, which releasably connects or couples vertical part 132 and substrate 141 to anterior head strap 54.

Figure 25:
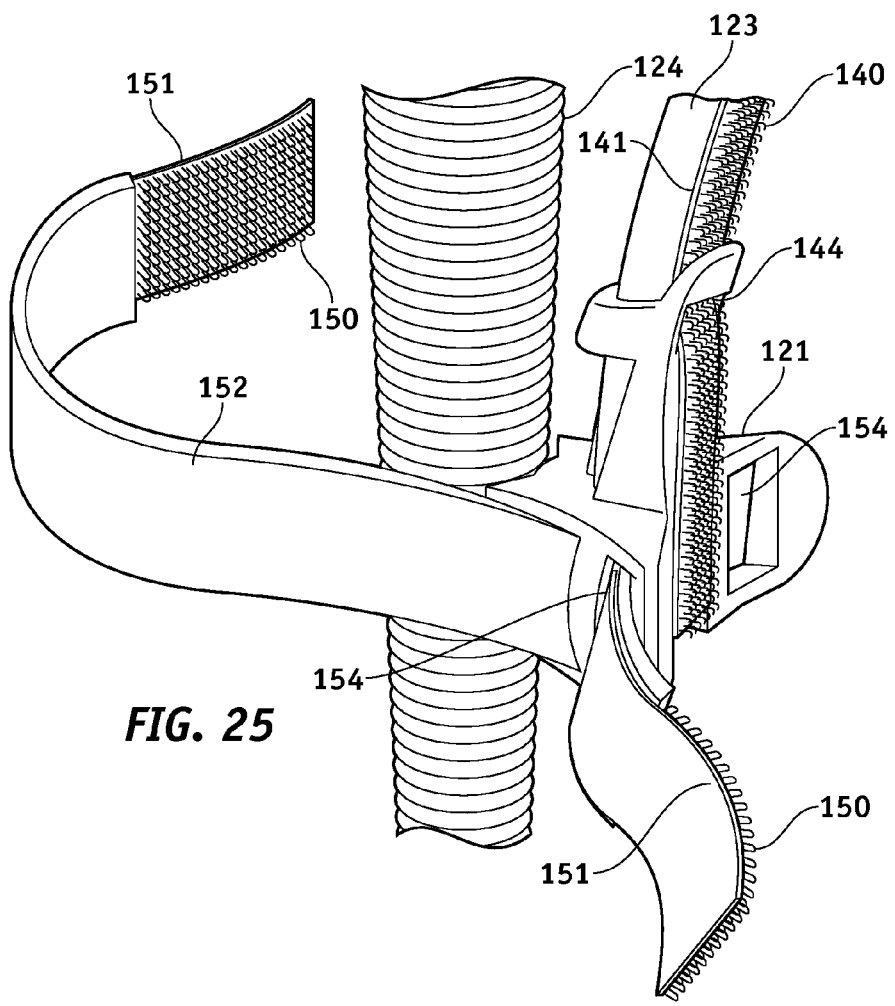
FIG. 25 is an enlarged fragmented perspective view of the ventilation therapy device of FIG. 18 illustrating the forehead anchor, a ventilation tube, and a strap shown as it would appear partially installed to the forehead anchor and the ventilation tube.

A loop fastener 150 again of the well-known type sold under the trademark VELCRO®, is carried by each of the two outer ends 151 of an elongate piece of fabric tape or other substrate 152, as shown in FIG. 25. Referencing FIGS. 18, 19, 22, 23, and 25 in relevant part, the middle of substrate 152 is applied over corrugated tube 124 as shown in FIGS. 18, 19, 22, and 23, and substrate 152 is concurrently threaded through opposed slotted openings 154 on either side of forehead anchor 121, and loop fasteners 150 of outer ends 151 of substrate 152 are pressed against the exposed portions of the respective hook fasteners 136 of horizontal part 131 of backing 130 on either side of forehead anchor 121 temporarily/releasably fastening outer ends 151 of substrate 151 to the outer sides of the outer ends of horizontal part 131 of backing 130 on either side of forehead anchor 121 in turn releasably embracing corrugated tube 124 against the outer side of forehead anchor 121.

Figure 23:
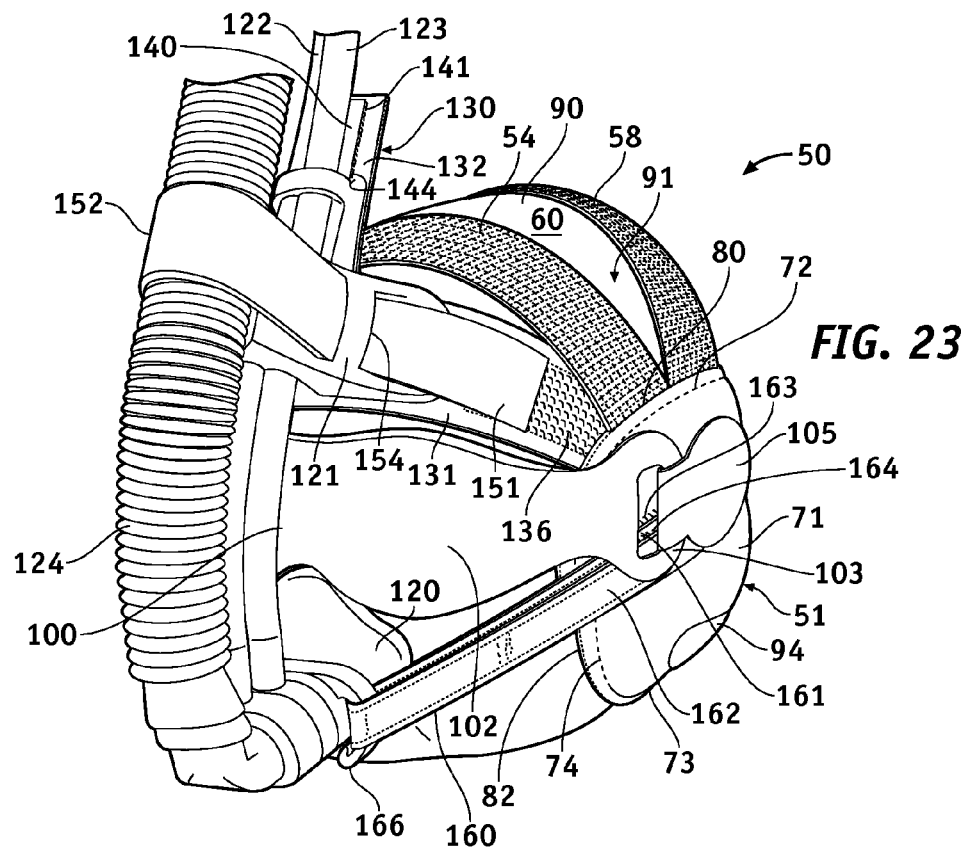
FIG. 23 is a right rear perspective view of the embodiment of FIG. 18.
Figure 24:
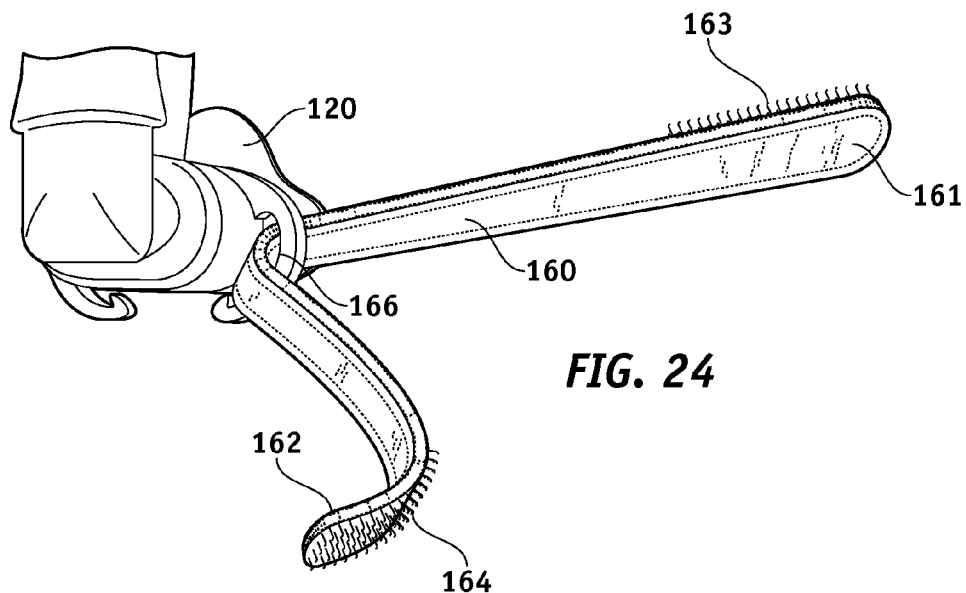
FIG. 24 is an enlarged fragmented perspective view of the ventilation therapy device of FIG. 18 illustrating a connecting strap applied to the ventilation mask.

Tubes 123 and 124 and corrugated tube 124, in turn, extend downwardly along the face of head 90 of infant 91 to ventilation mask 120, which is applied to infant's 91 nose and mouth so as to direct ventilating air to infant's 91 nose and mouth. Two identical fabric straps 160 releasably connected between ventilation mask 120 and left and right earguard pads 51 and 52 operatively anchor ventilation mask 120 relative to the nose and mouth of infant 91 to ensure the proper application of ventilating air to the nose and mouth of infant 91. Referencing FIGS. 19 and 22-24 in relevant part, fabric straps 160 are elongate and fashioned of cloth or clothlike material that hook fasteners can catch and cling to. Each strap 160 has opposed ends 161 and 162, and a pair of hook fasteners 163 and 164 each being of the well-known type sold under the trademark VELCRO®. Hook fastener 163 of each strap 160 is formed in the inner side of end 161, and hook fastener 164 of each strap is formed on the outer side of end 162. Clips 166 are formed on either side of ventilation mask 120. The middles of straps 160 are each threaded through the respective clips 166. Hook fasteners 163 of ends 161 of straps are each pressed against the respective outer sides 71 of left and right earguard pads 51 and 52 temporarily/releasably fastening ends 161 of the respective straps 160 to the outer sides 71 of the respective left and right earguard pads 51 and 52. Ends 162 of straps 160 are drawn tight away from ventilation mask 120 toward the respective left and right earguard pads 51 and 52 so as to draw ventilation mask against the nose and mouth of infant 91 so as to operatively position ventilation mask 120 relative to the nose and mouth of infant 91 to ensure ventilation air is properly applied to the nose and mouth of infant 91. Hook fasteners 164 of ends 162 of straps are each, in turn, pressed against the outer sides of ends 161 of the respective straps 160 temporarily/releasably fastening ends 162 of the respective straps 160 to ends 161 of the respective straps 160 so as to secure ventilation mask 120 in its operative position to deliver ventilation air to the nose and mouth of infant 91. Through this installation of CPAP 110 to headgear assembly 50 worn by head 90 of infant 91, CPAP device 110 is operatively anchored relative to the face of infant so as to deliver ventilating air to the nose and mouth of infant 91. After the completion of a therapy session, CPAP device 110 may be removed simply by reversing the above-described installation procedure. In the alternatively, one may simply tear backing 130 and straps 160 away from headgear assembly 50 for quick removal. As a matter of illustration and reference, FIG. 23 illustrates mask 100 and CPAP device 110 as they would appear releasably connected to headgear assembly 50 worn by head 90 of infant 91 so as to operatively anchor mask 100 and CPAP device 110 relative to the face of infant 91. The concurrently application of mask 100 and CPAP device 110 to headgear assembly 50 is useful for calming infant 91 during ventilation therapy.

The assembly of backing 130 and CPAP device 110 to headgear assembly 50 forms an exemplary embodiment of the invention. If desired, backing 130 can be connected to headgear assembly 50 first in preparation for installing CPAP device 110. The assembly of backing 130 to headgear assembly 50 forms an exemplary embodiment of the invention.

Figure 26:
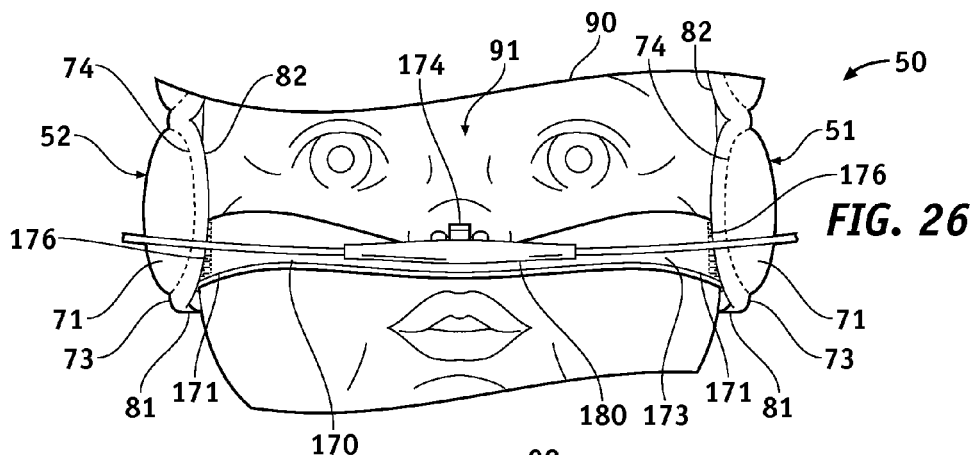
FIG. 26 is a fragmented, front elevation view of the headgear assembly of FIG. 1 shown as it would appear worn by a head of an infant, a backing connected to the left and right earguard pads and extending across the face of the infant, and a ventilation therapy device in the form of a nasal cannula applied over the backing.
Figure 29:
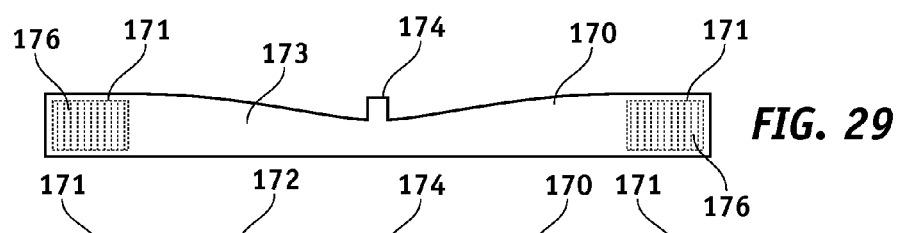
FIG. 29 is a front elevation view of the backing of FIG. 26.
Figure 30:
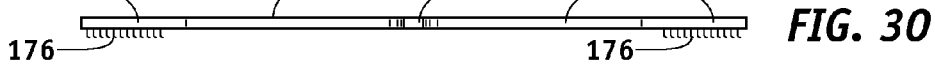
FIG. 30 is a top plan view of the backing of FIG. 26.

FIG. 26 is a fragmented, front elevation view of the headgear assembly 50 of FIG. 1 shown as it would appear worn by head 90 of infant 91, and another embodiment of a backing 170 connected to left and right earguard pads 51 and 52 and extending across the face of infant 91, and a ventilation therapy device in the form of a nasal cannula 180 applied over backing 170 and operatively positioned so as to deliver ventilation therapy to the nose of infant 91. Looking to FIGS. 29 and 30, backing 170 is formed of flat, soft, flexible material, such as flat soft, flexible cloth or clothlike material, is elongate, and has opposed outer ends 171, an inner side 172, an opposed outer side 173, and small tag 174 extending vertically upright from a middle of backing 170 between outer ends 171. A hook fastener 176 of the well-known type sold under the trademark VELCRO® is applied to the outer side of each of the opposed outer ends 171 of backing 170.

Figure 27:
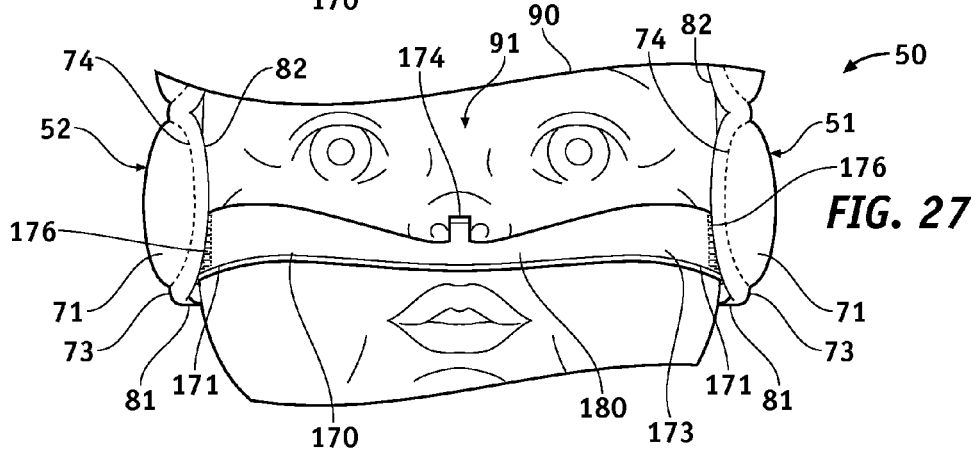
FIG. 27 is a view similar to that of FIG. 26 without the ventilation therapy device.
Figure 28:
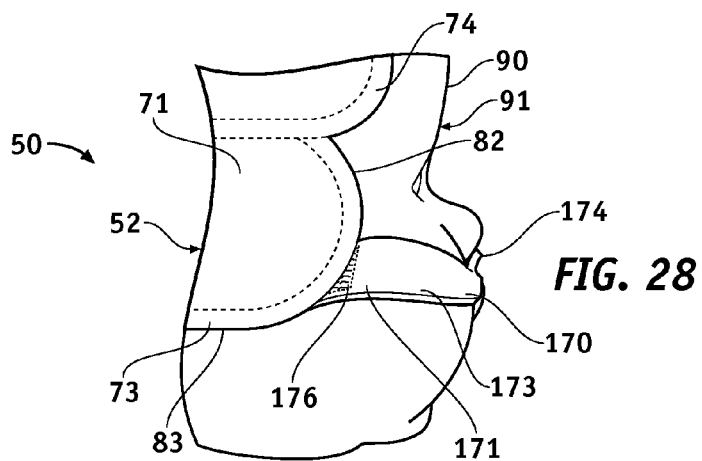
FIG. 28 is a left side elevation view of the embodiment of FIG. 27.

Looking in relevant part to FIGS. 26-28, backing 170 is releasably connected to headgear assembly 50 to operatively receive, as shown in FIG. 26, nasal cannula 180 relative to the nose of infant face of head 90 of infant 91. Specifically, with tag 174 directed upright inner side 172 of backing 170 is applied directly against the upper lip of infant 91 locating tag 174 on the underside of infant's 91 nose between his nostrils. Backing 170 is extended to across the face of infant 91 to outer end 171, which are tucked under inner sides 70 of left and right earguard pads 51 and 52 at fronts 74 of left and right earguard pads 51 and 52 near bottoms 73, respectively. Left and right earguard pads 51 and 52 are pressed against outer ends 171 of backing 170 so as to press inner sides 70 of left and right earguard pads 51 and 52 against the respective hook fasteners 176 temporarily/releasably fastening outer ends 171 of backing 170 to inner sides 70 of left and right earguard pads 51 and 52 in turn releasably connecting backing 170 to headgear assembly 50. With backing 170 releasably connected to headgear assembly 50 and operatively anchored across the upper lip and checks of the face of infant, nasal cannula 180 may be applied across outer side 173 of backing 170 and operatively applied to the nose of infant 91 to direct ventilation therapy to infant 91 via his nose. Backing 170 positioned between the upper lip and cheeks of the face of infant 91, including tag 174 located on the underside of infant's 91 nose between his nostrils, isolates nasal cannula 180 from directly contacting the upper lip and cheeks of the face of infant 91 and the underside of infant's 91 nose between his nostrils to ensure the comfort of infant 91. After the completion of a therapy session, nasal cannula 180 may be removed and backing 170 deunited from headgear assembly simply by reversing the above-described installation procedure, or by simply tear backing 170 away from headgear assembly 50 for quick removal.

The assembly of backing 170 and nasal cannula 180 to headgear assembly 50 forms an exemplary embodiment of the invention. If desired, backing 170 can be connected to headgear assembly 50 first in preparation for receiving nasal cannula 180. The assembly of backing 170 to headgear assembly 50 forms an exemplary embodiment of the invention.

The invention has been described above with reference to preferred embodiments. However, those skilled in the art will recognize that changes and modifications may be made to the embodiments without departing from the nature and scope of the invention. Various changes and modifications to the embodiments herein chosen for purposes of illustration will readily occur to those skilled in the art. To the extent that such modifications and variations do not depart from the spirit of the invention, they are intended to be included within the scope thereof.

Having fully described the invention in such clear and concise terms as to enable those skilled in the art to understand and practice the same, the invention claimed is:

1. An infant headgear assembly for operatively anchoring infant therapy devices in an application of therapy to an infant, the infant headgear assembly comprising:
   left and right earguard pads to provide noise suppression and ear protection, the left and right earguard pads are soft and cushiony and each includes an inner side, an opposed outer side, a top, a bottom, a front, and a rear;
   an elongate anterior head strap, an elongate posterior head strap, and an elongate middle head strap between the anterior head strap and the posterior head strap all connected to the left and right earguard pads attaching the left earguard pad to the right earguard pad, the left and right earguard pads and the anterior, posterior, and middle straps cooperate to define a head-receiving volume;
   the anterior head strap is connected to the top of the left earguard pad between the rear and the front thereof, and is connected to the top of the right earguard pad between the rear and the front thereof, and the anterior head strap is made of pliant, elastic, nonslip material;

the posterior head strap is connected to the rear of the left earguard pad between the top and the bottom thereof, and is connected to the rear of the right earguard pad between the top and the bottom thereof, and the posterior head strap is made of pliant, elastic, nonslip material;

the middle head strap is between the anterior head strap and the posterior head strap, the middle head strap is connected to the top of the left earguard pad between the rear thereof and the anterior head strap, and is connected to the top of the right earguard pad between the rear thereof and the anterior head strap, and the middle head strap is made of pliant, elastic, nonslip material;

the middle head strap extends vertically upward relative to the tops of the left and right earguard pads;

the posterior head strap extends horizontally rearward relative to the middle head strap from the rears of the left and right earguard pads;

the anterior head strap extends angularly upward relative to the tops of the left and right earguard pads, and extends angularly forward relative to the middle head strap;

the posterior head strap is connected to a majority of the rear of the left earguard pad from the bottom to the top thereof, and is connected to a majority of the rear of the right earguard pad from the bottom to the top thereof;

the posterior head strap is of maximum width nearer the rears of the left and right earguard pads and is of minimum width at a middle of the posterior head strap between the rears of the left and right earguards;

the posterior head strap includes a top edge and an opposed bottom edge, and the top edge is curved downwardly toward the bottom edge from the left and right earguard pads to the middle of the posterior head strap;

the inner side of the left earguard pad is configured to be positioned against a left side of a head of an infant for left ear noise suppression and left ear protection, the inner side of the right earguard pad is configured to be positioned against a right side of the head of the infant for right ear noise suppression and right ear protection, the anterior head strap is elastically stretched and is adapted to extend across and nonslip contact a frontal region of the head of the infant from the left earguard pad to the right earguard pad, the posterior head strap is elastically stretched and is adapted to extend across and nonslip contact an occipital region of the head of the infant from the left earguard pad to the right earguard pad, the middle head strap is elastically stretched and is adapted to extend across and nonslip contact a parietal region of the head of the infant from the left earguard pad to the right earguard pad, the inner sides of the left and right earguard pads and the outer sides of the left and right earguard pads are available to releasably connect therapy devices for operatively anchoring therapy devices relative to a face of an infant, the top edge of the posterior head strap curves downwardly toward the bottom edge from the left and right earguard pads to the middle of the posterior head strap so as to relate to a curvature of the occipital region of the head of the infant, the anterior, posterior, and middle head straps are configured to elastically constrict the headgear assembly to the left and right sides of the head of the infant, and the anterior, posterior, and middle head straps are adapted to nonslip contact the frontal, occipital, and parietal regions of the head of the infant, when the head of the infant is received in the head-receiving volume.

2. The infant headgear assembly according to claim 1, further comprising a first connector releasably connected between the posterior head strap and one of the left and right earguard pads taking up a first length of the posterior head strap so as to shorten the posterior head strap.

3. The infant headgear assembly according to claim 2, further comprising a second connector releasably connected between the posterior head strap and the other one of the left and right earguard pads taking up a second length of the posterior head strap so as to shorten the posterior head strap.

4. The infant headgear assembly according to claim 1, wherein the anterior and middle head straps each have a maximum width that is less than the minimum width of the posterior head strap.

5. An infant headgear assembly for operatively anchoring infant therapy devices in an application of therapy to an infant, the infant headgear assembly comprising:

left and right earguard pads to provide noise suppression and ear protection, the left and right earguard pads are soft and cushiony and each includes an inner side, an opposed outer side, and a parametric edge, the parametric edge includes an upper edge and a lower edge that extend between a rear edge and a front edge;

an elongate anterior head strap, an elongate posterior head strap, and an elongate middle head strap between the anterior head strap and the posterior head strap all connected to the left and right earguard pads attaching the left earguard pad to the right earguard pad, the left and right earguard pads and the anterior, posterior, and middle straps cooperate to define a head-receiving volume;

the anterior head strap is connected to the upper edge of the left earguard pad between the rear edge and the front edge thereof, and is connected to the upper edge of the right earguard pad between the rear edge and the front edge thereof, and the anterior head strap is made of pliant, elastic, nonslip material;

the posterior head strap is connected to the rear edge of the left earguard pad between the upper edge and the lower edge thereof, and is connected to the rear edge of the right earguard pad between the upper edge and the lower edge thereof, and the posterior head strap is made of pliant, elastic, nonslip material;

the middle head strap is between the anterior head strap and the posterior head strap, the middle head strap is connected to the upper edge of the left earguard pad between the rear edge thereof and the anterior head strap, and is connected to the upper edge of the right earguard pad between the rear edge thereof and the anterior head strap, and the middle head strap is made of pliant, elastic, nonslip material;

the middle head strap extends vertically upward relative to the upper edges of the left and right earguard pads;

the posterior head strap extends horizontally rearward relative to the middle head strap from the rear edges of the left and right earguard pads;

the anterior head strap extends angularly upward relative to the upper edges of the left and right earguard pads, and extends angularly forward relative to the middle head strap;

the posterior head strap is connected to a majority of the rear edge of the left earguard pad from the lower edge to the upper edge thereof, and is connected to a majority of the rear edge of the right earguard pad from the lower edge to the upper edge thereof;

the posterior head strap is of maximum width nearer the rear edges of the left and right earguard pads and is of minimum width at a middle of the posterior head strap between the rear edges of the left and right earguards;

the posterior head strap includes a top edge and an opposed bottom edge, and the top edge is curved downwardly toward the bottom edge from the left and right earguard pads to the middle of the posterior head strap;

the inner side of the left earguard pad is configured to be positioned against a left side of a head of an infant for left ear noise suppression and left ear protection, the inner side of the right earguard pad is configured to be positioned against a right side of the head of the infant for right ear noise suppression and right ear protection, the anterior head strap is elastically stretched and is adapted to extend across and nonslip contact a frontal region of the head of the infant from the left earguard pad to the right earguard pad, the posterior head strap is elastically stretched and is adapted to extend across and nonslip contact an occipital region of the head of the infant from the left earguard pad to the right earguard pad, the middle head strap is elastically stretched and is adapted to extend across and nonslip contact a parietal region of the head of the infant from the left earguard pad to the right earguard pad, the inner sides of the left and right earguard pads and the outer sides of the left and right earguard pads are available to releasably connect therapy devices for operatively anchoring therapy devices relative to a face of an infant, the top edge of the posterior head strap curves downwardly toward the bottom edge from the left and right earguard pads to the middle of the posterior head strap so as to relate to a curvature of the occipital region of the head of the infant; the anterior, posterior, and middle head straps are configured to elastically constrict the headgear assembly to the left and right sides of the head of the infant, and the anterior, posterior, and middle head straps are adapted to nonslip contact the frontal, occipital, and parietal regions of the head of the infant, when the head of the infant is received in the head-receiving volume.

6. The infant headgear assembly according to claim 5, further comprising a first connector releasably connected between the posterior head strap and one of the left and right earguard pads taking up a first length of the posterior head strap so as to shorten the posterior head strap.

7. The infant headgear assembly according to claim 6, further comprising a second connector releasably connected between the posterior head strap and the other one of the left and right earguard pads taking up a second length of the posterior head strap so as to shorten the posterior head strap.

8. The infant headgear assembly according to claim 5, wherein the anterior and middle head straps each have a maximum width that is less than the minimum width of the posterior head strap.

* * * * *